(12) United States Patent
Stead et al.

(10) Patent No.: US 7,767,152 B2
(45) Date of Patent: Aug. 3, 2010

(54) REAGENT CONTAINER AND SLIDE REACTION RETAINING TRAY, AND METHOD OF OPERATION

(75) Inventors: Ronald H. Stead, Bowmanville (CA); Xuan S. Bui, Culver City, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 756 days.

(21) Appl. No.: 11/346,876

(22) Filed: Feb. 3, 2006

(65) Prior Publication Data

US 2006/0171857 A1   Aug. 3, 2006

Related U.S. Application Data

(63) Continuation-in-part of application No. 10/639,021, filed on Aug. 11, 2003.

(60) Provisional application No. 60/652,170, filed on Feb. 11, 2005.

(51) Int. Cl.
*B01L 3/00* (2006.01)
*G01N 35/00* (2006.01)

(52) U.S. Cl. ............ 422/102; 422/99; 422/50; 422/63; 436/43; 436/46

(58) Field of Classification Search .......... 422/102, 422/99, 65; 436/46; 359/396
See application file for complete search history.

(56) References Cited

U.S. PATENT DOCUMENTS

| | | |
|---|---|---|
| 2,709,025 A | 5/1955 | Scott |
| 2,772,817 A | 12/1956 | Jauch |
| 3,294,290 A | 12/1966 | Erickson et al. |
| 3,904,079 A | 9/1975 | Kross |
| 4,018,363 A | 4/1977 | Cassia |
| 4,025,241 A | 5/1977 | Clemens |
| 4,039,775 A | 8/1977 | Andra |
| 4,099,483 A | 7/1978 | Henderson |
| 4,149,633 A | 4/1979 | Nilson |

(Continued)

FOREIGN PATENT DOCUMENTS

CN    2390207 Y    8/2000

(Continued)

OTHER PUBLICATIONS

European Search Report for EP Appln No. 06101498.1, mailed Jun. 20, 2006 (6 pages).

(Continued)

*Primary Examiner*—Walter D Griffin
*Assistant Examiner*—Christine T Mui
(74) *Attorney, Agent, or Firm*—Blakely Sokoloff Taylor & Zafman LLP

(57) ABSTRACT

A sample, or slide, retaining tray includes a reagent reservoir, or recess, and a reaction chamber. A slide, or other sample container, can be positioned on the sample retaining tray as desired, with a tissue specimen face down, between a platen on the tray and the slide. A reagent from the reservoir is rendered flowable, such as by heating, and flows from the reservoir into the reaction chamber. Optionally, reagents or other fluids can be provided from above, by dripping onto a drip surface of the sample retaining tray, or below via an inlet port in the platen.

21 Claims, 13 Drawing Sheets

U.S. PATENT DOCUMENTS

| | | |
|---|---|---|
| 4,199,558 A | 4/1980 | Henderson |
| 4,234,089 A | 11/1980 | Morris |
| 4,254,880 A | 3/1981 | Mangel |
| 4,258,759 A | 3/1981 | Achen |
| 4,335,673 A | 6/1982 | Fixot |
| 4,338,738 A | 7/1982 | Lamb |
| 4,356,727 A | 11/1982 | Brown et al. |
| 4,513,438 A | 4/1985 | Graham et al. |
| 4,604,964 A | 8/1986 | Gordon et al. |
| 4,667,854 A | 5/1987 | McDermott et al. |
| 4,673,109 A | 6/1987 | Cassia |
| 4,678,752 A | 7/1987 | Thorne et al. |
| 4,682,890 A | 7/1987 | de Macario et al. |
| 4,731,335 A | 3/1988 | Brigati |
| 4,741,898 A | 5/1988 | Mallik et al. |
| 4,764,342 A | 8/1988 | Kelln et al. |
| 4,790,640 A * | 12/1988 | Nason ..................... 359/396 |
| 4,798,311 A | 1/1989 | Workum |
| 4,801,431 A | 1/1989 | Cuomo et al. |
| 4,834,019 A | 5/1989 | Gordon et al. |
| 4,838,457 A | 6/1989 | Swahl et al. |
| 4,846,636 A | 7/1989 | Danby et al. |
| 4,867,347 A | 9/1989 | Wass et al. |
| 4,880,149 A | 11/1989 | Scholefield et al. |
| 4,886,192 A | 12/1989 | Cassia |
| 4,921,136 A | 5/1990 | Roggenburg, Jr. |
| 4,927,061 A | 5/1990 | Leigh et al. |
| 4,946,076 A | 8/1990 | Hackmann et al. |
| 4,955,512 A | 9/1990 | Sharples |
| 4,961,508 A | 10/1990 | Weimer et al. |
| 4,969,581 A | 11/1990 | Seifert et al. |
| 4,972,978 A | 11/1990 | DeLuca |
| 4,974,754 A | 12/1990 | Wirz |
| 4,978,036 A | 12/1990 | Burd |
| 4,985,206 A | 1/1991 | Bowman et al. |
| 5,002,736 A | 3/1991 | Babbitt et al. |
| 5,009,185 A | 4/1991 | Stokes et al. |
| 5,033,656 A | 7/1991 | Blette et al. |
| 5,035,350 A | 7/1991 | Blette et al. |
| 5,040,837 A | 8/1991 | Ozeki |
| 5,068,091 A | 11/1991 | Toya |
| 5,082,150 A | 1/1992 | Steiner et al. |
| 5,225,325 A | 7/1993 | Miller et al. |
| 5,232,664 A | 8/1993 | Krawzak et al. |
| 5,242,083 A | 9/1993 | Christine et al. |
| 5,244,787 A | 9/1993 | Key et al. |
| 5,252,293 A | 10/1993 | Drbal et al. |
| 5,273,905 A * | 12/1993 | Muller et al. ............ 435/286.5 |
| 5,275,309 A | 1/1994 | Baron et al. |
| 5,316,452 A | 5/1994 | Bogen et al. |
| 5,322,771 A | 6/1994 | Rybski et al. |
| 5,338,358 A | 8/1994 | Mizusawa et al. |
| 5,355,439 A | 10/1994 | Bernstein et al. |
| 5,356,039 A | 10/1994 | Christine et al. |
| 5,418,138 A | 5/1995 | Miller et al. |
| 5,424,036 A | 6/1995 | Ushikubo |
| 5,425,918 A | 6/1995 | Healey et al. |
| 5,433,351 A | 7/1995 | Okuyama et al. |
| 5,439,649 A | 8/1995 | Tseung et al. |
| 5,441,894 A | 8/1995 | Coleman et al. |
| 5,561,556 A | 10/1996 | Weissman |
| 5,578,452 A | 11/1996 | Shi et al. |
| 5,580,523 A | 12/1996 | Bard |
| 5,595,707 A | 1/1997 | Copeland et al. |
| 5,602,674 A | 2/1997 | Weissman et al. |
| 5,609,822 A | 3/1997 | Carey et al. |
| 5,626,262 A | 5/1997 | Fitten et al. |
| 5,645,114 A | 7/1997 | Bogen et al. |
| 5,650,327 A | 7/1997 | Copeland et al. |
| 5,654,200 A | 8/1997 | Copeland et al. |
| 5,675,715 A | 10/1997 | Bernstein et al. |
| 5,700,346 A | 12/1997 | Edwards |
| 5,810,204 A | 9/1998 | Devlin et al. |
| 5,839,091 A | 11/1998 | Rhett et al. |
| 5,843,700 A | 12/1998 | Kerrod et al. |
| 5,846,396 A | 12/1998 | Zanzucchi et al. |
| 5,851,488 A | 12/1998 | Saul et al. |
| 5,855,302 A | 1/1999 | Fisscher |
| 5,857,595 A | 1/1999 | Nilson |
| 5,885,530 A | 3/1999 | Babson et al. |
| 5,947,167 A | 9/1999 | Bogen et al. |
| 5,948,359 A * | 9/1999 | Kalra et al. .................. 422/65 |
| 5,950,874 A | 9/1999 | Sindoni |
| 5,950,878 A | 9/1999 | Wade et al. |
| 5,954,167 A | 9/1999 | Richardson et al. |
| 5,964,454 A | 10/1999 | Volpel |
| 5,965,454 A | 10/1999 | Farmilo et al. |
| 5,968,731 A | 10/1999 | Layne et al. |
| 5,971,223 A | 10/1999 | Fisscher |
| 6,001,309 A | 12/1999 | Gamble et al. |
| 6,020,995 A | 2/2000 | Dreyer et al. |
| 6,045,759 A | 4/2000 | Ford et al. |
| 6,076,583 A | 6/2000 | Edwards |
| 6,092,695 A | 7/2000 | Loeffler |
| 6,093,574 A | 7/2000 | Druyor-Sanchez et al. |
| 6,096,271 A | 8/2000 | Bogen et al. |
| 6,118,582 A | 9/2000 | Del Buono |
| 6,180,061 B1 | 1/2001 | Bogen et al. |
| 6,183,693 B1 | 2/2001 | Bogen et al. |
| 6,189,740 B1 | 2/2001 | Wade et al. |
| 6,192,945 B1 | 2/2001 | Ford et al. |
| 6,216,916 B1 | 4/2001 | Maddox et al. |
| 6,238,910 B1 | 5/2001 | Custance et al. |
| 6,244,474 B1 | 6/2001 | Loeffler |
| 6,259,956 B1 | 7/2001 | Myers et al. |
| 6,273,298 B1 | 8/2001 | Post |
| 6,296,809 B1 | 10/2001 | Richards et al. |
| 6,335,166 B1 | 1/2002 | Ammann et al. |
| 6,343,716 B1 | 2/2002 | Baudin et al. |
| 6,349,264 B1 | 2/2002 | Rhett et al. |
| 6,352,861 B1 | 3/2002 | Copeland et al. |
| 6,387,326 B1 | 5/2002 | Edwards et al. |
| 6,415,961 B2 | 7/2002 | Bonningue |
| 6,416,713 B1 | 7/2002 | Ford et al. |
| 6,451,551 B1 | 9/2002 | Zhan et al. |
| 6,472,217 B1 | 10/2002 | Richards et al. |
| 6,495,106 B1 | 12/2002 | Kalra et al. |
| 6,516,620 B2 | 2/2003 | Lang |
| 6,540,117 B2 | 4/2003 | Powling |
| 6,541,261 B1 | 4/2003 | Bogen et al. |
| 6,543,652 B1 | 4/2003 | Kelder et al. |
| 6,544,798 B1 | 4/2003 | Christensen et al. |
| 6,553,145 B1 | 4/2003 | Kang et al. |
| 6,580,056 B1 | 6/2003 | Tacha |
| 6,582,962 B1 | 6/2003 | Richards et al. |
| 6,594,537 B1 | 7/2003 | Bernstein et al. |
| 6,605,213 B1 | 8/2003 | Ammann et al. |
| 6,607,103 B2 | 8/2003 | Gerenraich et al. |
| 6,632,598 B1 | 10/2003 | Zhang et al. |
| 6,635,225 B1 | 10/2003 | Thiem et al. |
| 6,673,620 B1 * | 1/2004 | Loeffler et al. ................ 436/46 |
| 6,720,888 B2 | 4/2004 | Eagleson et al. |
| 6,729,502 B2 | 5/2004 | Lewis et al. |
| 6,735,531 B2 | 5/2004 | Rhett et al. |
| 6,746,851 B2 | 6/2004 | Tseung et al. |
| 6,758,360 B2 | 7/2004 | Van Giezen et al. |
| 6,783,733 B2 | 8/2004 | Bogen et al. |
| 6,827,900 B2 | 12/2004 | Thiem et al. |
| 6,827,901 B2 | 12/2004 | Copeland et al. |
| 6,855,552 B2 | 2/2005 | Towne et al. |
| 6,855,559 B1 | 2/2005 | Christensen et al. |
| 6,899,283 B2 | 5/2005 | Ohnishi et al. |
| 6,943,029 B2 | 9/2005 | Copeland et al. |
| 6,945,128 B2 | 9/2005 | Ford et al. |

| | | |
|---|---|---|
| 6,991,934 B2 | 1/2006 | Walton et al. |
| 6,998,270 B2 | 2/2006 | Tseung et al. |
| 7,007,824 B2 | 3/2006 | Danby et al. |
| 7,070,951 B2 | 7/2006 | Zhang et al. |
| 7,083,106 B2 | 8/2006 | Albany |
| 7,118,918 B2 | 10/2006 | Copeland et al. |
| 7,165,722 B2 | 1/2007 | Shafer et al. |
| 7,178,416 B2 | 2/2007 | Whelan et al. |
| 7,179,424 B2 | 2/2007 | Williamson, IV et al. |
| 7,187,286 B2 | 3/2007 | Morris et al. |
| 7,199,712 B2 | 4/2007 | Tafas et al. |
| 7,201,295 B1 | 4/2007 | Sitzberger |
| 7,209,042 B2 | 4/2007 | Martin et al. |
| 7,217,392 B2 | 5/2007 | Bogen et al. |
| 7,220,589 B2 | 5/2007 | Richards et al. |
| 7,226,788 B2 | 6/2007 | De La Torre-Bueno |
| 7,233,250 B2 | 6/2007 | Forster |
| 7,264,142 B2 | 9/2007 | Py |
| 7,270,785 B1 | 9/2007 | Lemme et al. |
| 7,275,682 B2 | 10/2007 | Excoffier et al. |
| 7,278,554 B2 | 10/2007 | Armstrong |
| 7,303,725 B2 | 12/2007 | Reinhardt et al. |
| 7,314,238 B2 | 1/2008 | Robert |
| 7,323,491 B2 | 1/2008 | Lohray et al. |
| 7,338,803 B2 | 3/2008 | Mizzer et al. |
| 7,382,258 B2 | 6/2008 | Oldham et al. |
| 7,395,974 B2 | 7/2008 | Albany |
| 7,405,056 B2 | 7/2008 | Lam et al. |
| 7,435,383 B2 | 10/2008 | Tseung et al. |
| 7,449,153 B2 | 11/2008 | Sakai et al. |
| 7,468,161 B2 | 12/2008 | Reinhardt et al. |
| 7,470,401 B2 | 12/2008 | Morales |
| 7,470,541 B2 | 12/2008 | Copeland et al. |
| 2001/0044603 A1 | 11/2001 | Harrold |
| 2002/0013194 A1 | 1/2002 | Kitano et al. |
| 2002/0030598 A1 | 3/2002 | Dombrowski et al. |
| 2002/0079318 A1 | 6/2002 | Wurzinger |
| 2002/0114733 A1 | 8/2002 | Copeland et al. |
| 2003/0100043 A1 | 5/2003 | Kalra et al. |
| 2003/0157545 A1 | 8/2003 | Jevons et al. |
| 2003/0203493 A1 | 10/2003 | Lemme et al. |
| 2004/0033163 A1 | 2/2004 | Tseung et al. |
| 2004/0091395 A1 | 5/2004 | Ward et al. |
| 2004/0120862 A1 | 6/2004 | Lang et al. |
| 2004/0191128 A1 | 9/2004 | Bogen et al. |
| 2004/0197230 A1 | 10/2004 | Lemme et al. |
| 2004/0266015 A1 | 12/2004 | Favuzzi et al. |
| 2005/0019902 A1 | 1/2005 | Mathies et al. |
| 2005/0035156 A1 | 2/2005 | Hersch et al. |
| 2005/0064535 A1 | 3/2005 | Favuzzi et al. |
| 2005/0135972 A1 | 6/2005 | Lemme et al. |
| 2005/0150911 A1 | 7/2005 | Bach |
| 2005/0153453 A1 | 7/2005 | Copeland et al. |
| 2005/0164374 A1 | 7/2005 | Kram |
| 2005/0186114 A1 | 8/2005 | Reinhardt et al. |
| 2005/0191214 A1 | 9/2005 | Tseung et al. |
| 2005/0250211 A1 | 11/2005 | Reinhardt et al. |
| 2005/0281711 A1 | 12/2005 | Testa et al. |
| 2006/0019332 A1 | 1/2006 | Zhang et al. |
| 2006/0040341 A1 | 2/2006 | Bland et al. |
| 2006/0045806 A1 | 3/2006 | Winther et al. |
| 2006/0063265 A1 | 3/2006 | Welcher et al. |
| 2006/0088928 A1 | 4/2006 | Sweet et al. |
| 2006/0088940 A1 | 4/2006 | Feingold et al. |
| 2006/0105359 A1 | 5/2006 | Favuzzi et al. |
| 2006/0120921 A1 | 6/2006 | Elliot et al. |
| 2006/0127283 A1 | 6/2006 | Tseung et al. |
| 2006/0134793 A1 | 6/2006 | Key et al. |
| 2006/0147351 A1 | 7/2006 | Falb et al. |
| 2006/0148063 A1 | 7/2006 | Fauzzi et al. |
| 2006/0159367 A1 | 7/2006 | Zeineh et al. |
| 2006/0171857 A1 | 8/2006 | Stead et al. |
| 2006/0190185 A1 | 8/2006 | Ford et al. |
| 2006/0191952 A1 | 8/2006 | Kalra et al. |
| 2006/0239867 A1 | 10/2006 | Schaeffer |
| 2006/0252025 A1 | 11/2006 | Nitta et al. |
| 2006/0263268 A9 | 11/2006 | Tseung et al. |
| 2006/0265133 A1 | 11/2006 | Cocks et al. |
| 2006/0269985 A1 | 11/2006 | Kitayama |
| 2007/0010912 A1 | 1/2007 | Feingold et al. |
| 2007/0038491 A1 | 2/2007 | Samuhel et al. |
| 2007/0160494 A1 | 7/2007 | Sands |
| 2007/0171070 A1 | 7/2007 | Tafas et al. |
| 2007/0270714 A1 | 11/2007 | Cushner et al. |
| 2007/0279735 A1 | 12/2007 | Sieckmann |
| 2007/0292315 A1 | 12/2007 | Patenaude et al. |
| 2008/0069736 A1 | 3/2008 | Mingerink et al. |
| 2008/0102006 A1 | 5/2008 | Kram et al. |
| 2008/0113440 A1 | 5/2008 | Gurney et al. |
| 2008/0213902 A1 | 9/2008 | Ichetovkin et al. |
| 2008/0215625 A1 | 9/2008 | Veitch et al. |
| 2008/0235055 A1 | 9/2008 | Mattingly et al. |
| 2008/0238674 A1 | 10/2008 | Tafas et al. |
| 2008/0239478 A1 | 10/2008 | Tafas et al. |
| 2008/0254503 A1 | 10/2008 | Ljungmann et al. |
| 2008/0284602 A1 | 11/2008 | Morris et al. |
| 2008/0286753 A1 | 11/2008 | Erickson et al. |
| 2008/0305515 A1 | 12/2008 | Burgart et al. |

FOREIGN PATENT DOCUMENTS

| | | |
|---|---|---|
| DE | 3902476 | 8/1990 |
| EP | 0185330 | 6/1986 |
| EP | 0557871 | 9/1993 |
| EP | 1028320 | 8/2000 |
| EP | 1333287 | 8/2003 |
| FR | 2541244 | 2/1983 |
| GB | 2037255 | 7/1980 |
| JP | 6-510860 | 12/1994 |
| JP | 9-503060 | 3/1997 |
| JP | 10-501167 | 2/1998 |
| JP | 2000167318 | 6/2000 |
| JP | 2001-509727 | 7/2001 |
| JP | 2001-512823 | 8/2001 |
| JP | 2001-522033 | 11/2001 |
| JP | 2002-522065 | 7/2002 |
| JP | 2003-057246 | 2/2003 |
| JP | 2004-533605 | 11/2004 |
| WO | WO 95/08774 | 3/1995 |
| WO | WO 95/26796 | 10/1995 |
| WO | WO 96/39260 | 12/1996 |
| WO | WO 99/08090 | 2/1999 |
| WO | WO 99/22867 | 5/1999 |
| WO | WO 00/09650 | 2/2000 |
| WO | WO 00/12994 | 3/2000 |
| WO | WO 01/41918 | 6/2001 |
| WO | WO-01/54813 | 8/2001 |
| WO | WO 02/072264 A1 | 9/2002 |
| WO | WO 03/054553 | 7/2003 |
| WO | WO-03/061453 | 7/2003 |
| WO | WO-03/064670 | 8/2003 |
| WO | WO 03/091710 | 11/2003 |
| WO | WO 03/106033 A1 | 12/2003 |
| WO | WO 2004/059288 | 7/2004 |
| WO | WO-2004/074845 | 9/2004 |
| WO | WO 2004/074847 | 9/2004 |
| WO | WO 2005/000731 | 1/2005 |

OTHER PUBLICATIONS

European Search Report for EP Appln No. 06101495.7, mailed Dec. 18, 2006 (10 pages).
PCT Search Report for PCT Appln No. PCT/US04/25960, mailed Aug. 8, 2006 (10 pages).
PCT Search Report for PCT Appln No. PCT/US2007/012400, mailed Nov. 16, 2007 (13 pages).

Zhang, Guangrong, et al., "Deparaffinization compositions and methods for their use," U.S. Appl. No. 11/250,142, filed Oct. 13, 2005.

Shi, Shan-Rong, et al., "Enhancement of immunochemical staining in aldehyde-fixed tissue," U.S. Appl. No. 11/249,180, filed Oct. 11, 2005.

Office Action for Japanese Application No. 2006-34547 dated Dec. 26, 2008 (7 pages).

Office Action for Chinese Application No. 200610007366.7 dated May 8, 2009 (21 pages).

* cited by examiner

Section B-B

Detail C

REAGENT CONTAINER AND SLIDE REACTION RETAINING TRAY, AND METHOD OF OPERATION

Priority is claimed to U.S. Provisional Patent Application Ser. No. 60/652,170, entitled "Reagent Container and Slide Reaction And Retaining Tray, And Method of Operation, filed Feb. 11, 2005, the contents of each of which are incorporated in their entireties herein by reference. This application also is a continuation-in-part of co-pending U.S. patent application Ser. No. 10/639,021, filed on Aug. 11, 2003, and entitled "Fluid Dispensing Apparatus", which is incorporated herein by reference in its entirety.

FIELD OF THE INVENTION

The present invention is directed generally to a tissue sample processing system and, in particular, to a sample retaining tray used in such a system.

BACKGROUND OF THE INVENTION

Tissue processors can be operated with varying levels of automation to process human or animal tissue specimens for histology or pathology uses. Various types of chemical reagents can be used at various stages of tissue processing and various systems have been developed for delivering reagents to specimen containing slides. Examples of known reagent delivery systems include small quantity release dispensers, manual pouring into reagent vats, or via bulk containers connected with a processor via tubing.

There are various disadvantages of known systems. For example, manually pouring into, or draining, reagent vats is time consuming and requires pouring accuracy, thereby decreasing the overall efficiency of the tissue processing system. Another disadvantage is that manually pouring and draining reagents can be sloppy, requiring clean-up of spills and consequential instrument down-time. A further disadvantage is that selecting the correct reagent requires operator attention and accuracy and there is an increased possibility of reagent application errors, resulting in a decrease in test accuracy and operational efficiency.

Automated systems also present various disadvantages. Reagents need to be selected and administered to slides during processing. The reagents frequently need to be delivered via gravity promoted dispensing from above. Such delivery systems require specialized equipment for reagent delivery such as specialized reagent dispensers or drivers or automated pipetting systems. Such systems suffer various drawbacks such as the amount of effort required to set up and dispense the reagents, the possibilities of evaporation during processing or contamination and difficulties in handling minute quantities of large numbers of reagents.

One known slide retaining tray and system for staining tissues is described in U.S. Pat. No. 5,338,358, which is incorporated herein by reference. As illustrated in that patent, a platen is provided and various mounting elements are provided to mount a slide on the slide tray. Space for five slides is illustrated. A reaction chamber is provided between a platen surface and a slide mounted on the tray. Reagents are introduced into the reaction chamber via drip surfaces and attendant capillary action. Additional known slide retaining trays and systems are described in U.S. Pat. Nos. 5,695,942 and 5,965,545, which are incorporated herein by reference. As illustrated in those patents, individually heated or cooled slide retaining apparatus are provided. The slides are positioned adjacent a surface and reagents can be introduced between the slides and their respective surfaces, such as by melting a gel containing a reagent by heating.

SUMMARY OF THE INVENTION

The present invention alleviates to a great extent the disadvantages of the known automated slide staining systems by providing a sample retaining tray and reaction chamber that may be utilized in a tissue processing system. Preferably, the sample retaining tray provides a reaction chamber and optionally retains a reagent or plural reagents in one or more reagent reservoirs. In an embodiment, the retaining tray includes a platen, a drip surface and a recess that acts as a reagent container. The reagent container may house a reagent or combination of reagents, such as a primary reagent used in processing a substrate. The reagent housed within the tray will be referred to herein as a "recess reagent."

The platen and other structural features of the tray preferably orient a slide positioned on the tray in such a way that a reaction chamber is formed between all or a portion of the platen and the slide surface. The reaction chamber may be configured so that reagents can be delivered into the reaction chamber, while the slide is in position. The substrate can be any item that is desired to be processed, such as a human or animal tissue that is sectioned. The retaining tray is preferably disposable after a single use, although multiple uses are possible as well with the same system. According to some embodiments, the retaining tray may be provided with an identifier that provides information concerning the reagent(s) contained within the tray, or the type of tray where multiple tray types may be used in a system.

In an embodiment, the reagent in the reagent recess is provided in a fluidizable matrix, such as a gel or meltable solid. A system using the retaining tray preferably includes a temperature controlling system, such as including a heating and/or cooling element positioned so as to provide heat or cool to the reagent recess as desired such as to heat the reagent so as to liquefy it sufficiently for it to flow as desired into the reaction chamber, from the reagent recess. The heating and/or cooling element(s) optionally are disposed substantially beneath the bottom surface. In addition, the heating and/or cooling elements can be used to control reaction kinetics, and to cool the reagent matrix in the reagent chamber so as to retain the reagent matrix in a solid, gel or other non-flowable form, such as to counteract the heat levels generated by an instrument.

Other reagents for processing the substrate may be dispensed onto a drip surface that is configured to receive the reagents dispensed from above, and then direct the reagent(s) to flow as desired, such as into the reaction chamber formed between the platen and the slide. The external reagents, which are applied from external sources, can be secondary reagents, primary reagents or any other fluid desired to be applied. Reagents supplied from external sources will be referred to herein as "external reagents".

A removable barrier or seal may be used to cover the reagent containing recess. The barrier or seal preferably is relatively vapor and fluid impermeable, and covers any otherwise open portions of the recess, such as the top and one or more side surfaces. In an alternative embodiment, a side surface of the recess is blocked with a slidable barrier that can be slid out of blocking engagement as desired, and then slid back if desired.

In an embodiment, the reagent containing recess is refillable. For example, the recess optionally includes a bottom surface having one or more apertures for supplying a predetermined amount of a matrix containing the recess reagent to the recess. Any other filling mechanism that can fill the recess as desired also can be used, such as re-loading the recess reagent, such as a primary reagent, into the recess from above. The reagent can be positioned into the recess in refilling in any form, such as caplets, one or more pellets, dripping, pouring, or squeezing from a tube.

Fluids and reagents also can be introduced into the system by other means. In one embodiment, fluids and/or reagents are introduced, and/or evacuated from below. One example is by providing one or more fluid entry ports in the platen and optionally one or more fluid evacuation ports also in the platen. Preferably the entry and evacuation ports are at generally opposite ends of the platen so as to create a fluid flow gradient from one end to the other end of the platen. With a slide positioned in the tray, the reaction chamber is formed between the slide and platen, with a fluid flow gradient from one end to the other. In one embodiment, each of the fluid entry and evacuation ports have plural holes, that are relatively small, so that they act as a screen. Optionally, a screen can be positioned on the ports.

The size of the space between the tray platen and slide can be configured to create fluid flow properties as desired. In an embodiment, the reaction chamber width (i.e. distance between platen and slide) is thin enough so as to promote capillary action induced fluid flow from one end to the other. Preferably the fluid flow is from the reagent recess end towards the opposite end. In this way, reagents flow via capillary action from the recess towards the opposite end of the reaction chamber. Moreover, secondary or other reagents introduced from above onto a drip surface also may be induced to flow from one end to the other. Likewise fluids introduced from below via the fluid entry port may be induced to flow via capillary action. In that way, assistance from a pressure gradient created from the evacuation port is not required, although optionally can be used as well. In another embodiment, the reaction chamber width may be selected so as to prevent capillary action. In such an embodiment, directed fluid flow can be achieved such as via gravity or via pressure differentials between input and evacuation ports.

In another aspect of the invention, the platen is elevated above a bottom surface of the tray. The space formed between the side walls of the platen, the walls of the tray, and the bottom of the tray can retain fluid overflow from the platen and reaction chamber. In addition, that space may be used to mix reagents before drawing them onto the platen. Such fluids can be evacuated via the evacuation port(s).

Another aspect of the present invention involves a substrate processing system able to utilize multiple retaining trays. The system further includes fluid handling systems, such as a pipetting system or dispensing assembly that dispenses external reagents from above onto the tray drip surfaces as desired. Likewise, optionally a fluid manifold is provided for directing multiple different fluids from below to the entry ports and for directing waste fluid(s) as desired from the evacuation ports to one or more waste fluid containers.

A further aspect of the present invention involves a method of using a tray for retaining a slide having a substrate attached thereto, wherein one or more reagents are provided into the reaction chamber from a reagent recess via flow from the recess into the reaction chamber, optionally induced by heating the recess. Optionally additional reagents can be dispensed from above onto a drip surface that is oriented to allow the fluid to flow into the reaction chamber as well. Additionally, fluids can be provided from below via the entry port(s) and evacuated via the evacuation port(s). It should be understood that any ordering of these options may be selected, and any number of reagents can be selected—whether single or multiple bulk reagents, external reagents or recess reagents.

An additional aspect of the present invention involves a method of manufacturing a tray for retaining a slide having a substrate attached thereto, wherein the tray houses a recess reagent to be used in processing the substrate. The method includes the steps of fabricating the tray to include a recess, dispensing a desired quantity of a matrix containing a reagent into the recess, sealing the recess and applying a machine readable identifier to the tray.

These and other features and advantages of the present invention will be appreciated from review of the following detailed description of the invention, along with the accompanying figures in which like reference numerals refer to like parts throughout.

DETAILED DESCRIPTION

Figure 1:
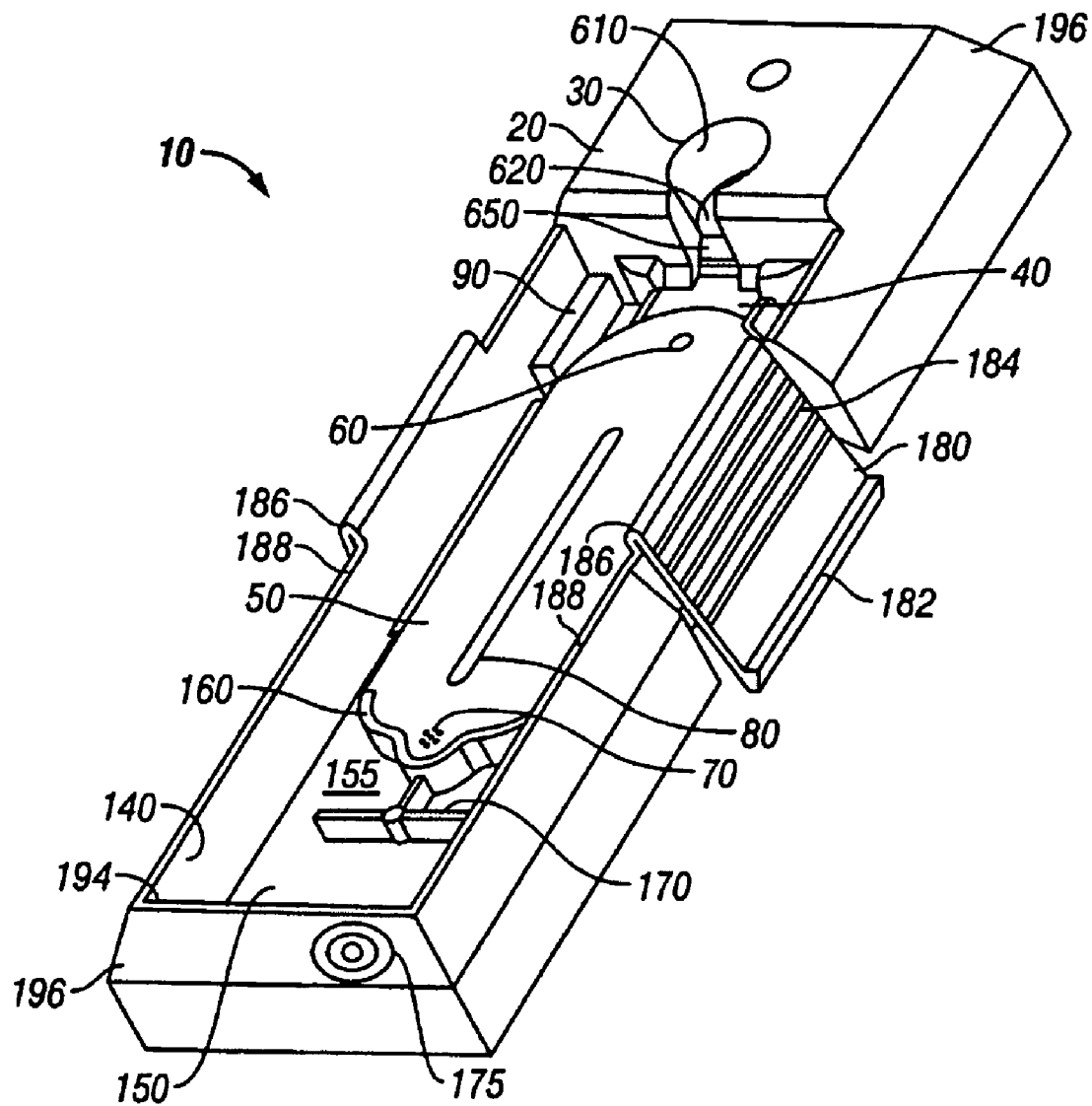
FIG. 1 is a top perspective view of a slide retaining tray in accordance with the present invention.
Figure 2:
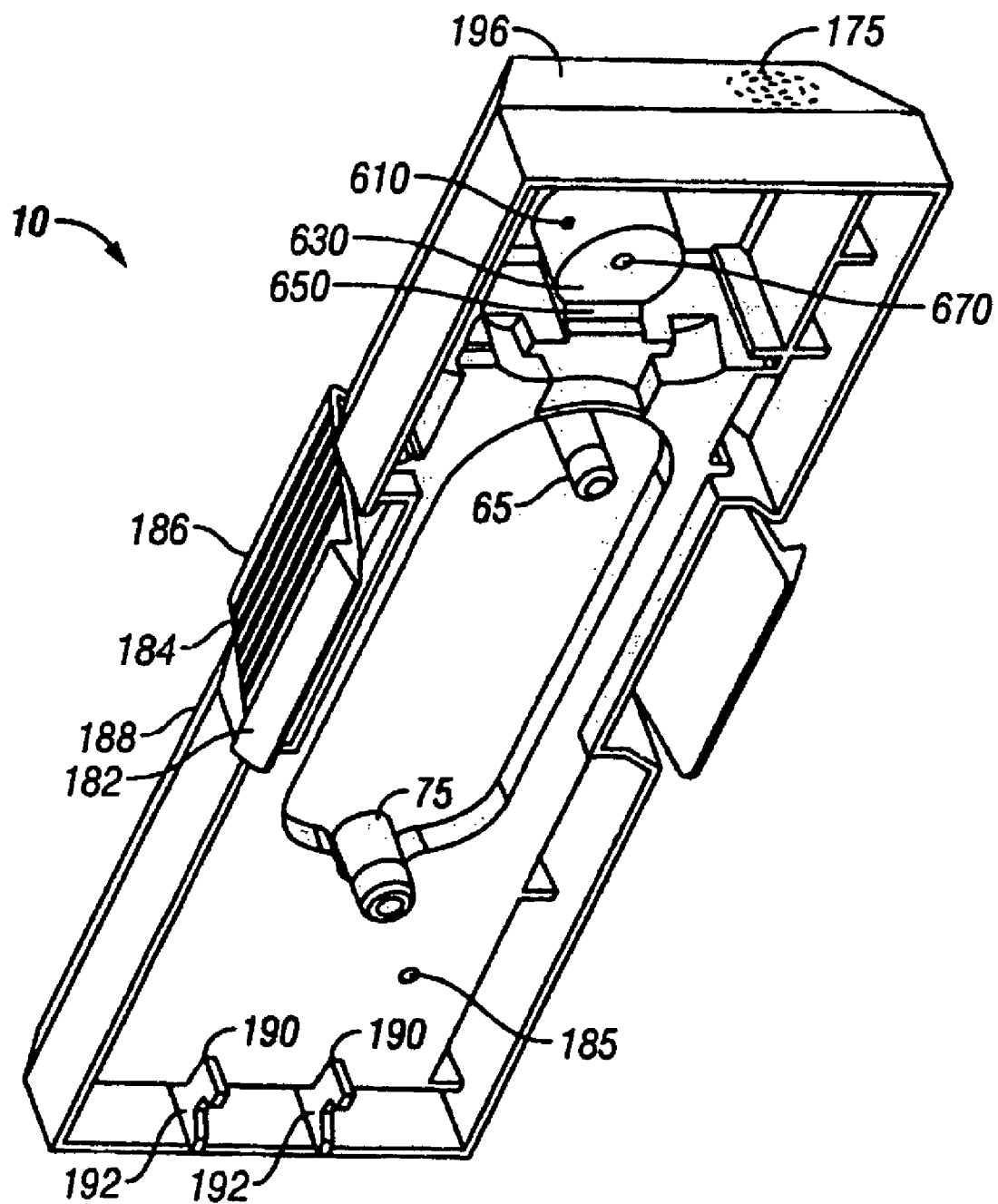
FIG. 2 is a bottom perspective view of a slide retaining tray in accordance with the present invention.

In the following paragraphs, the present invention will be described in detail by way of example with reference to the figures. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

A sample or slide retaining tray 10 in accordance with the principles of the present invention is illustrated in the figures and described in the following paragraphs. As used herein the terms sample retaining tray and slide retaining tray are used interchangeably for a retaining tray 10 that can retain a sample and/or slide. In the illustrated embodiment, sample retaining tray 10 is configured to be a microscope slide retaining tray 10 but it shall be appreciated that sample retaining tray is not so limited and may be configured to retain any sample or sample container. In accordance with an aspect of the present invention, slide retaining tray 10 functions as a reagent container, a reaction chamber and a slide positioning and retention system that may be used in processing a substrate such as a tissue sample.

In one embodiment, the slide retaining tray 10 is disposable after a single use, although it also can be used multiple times and the reagent container can be refillable. Optionally, the slide retaining tray 10 can include an identifier that is human or machine readable. Examples of identifiers can be visually readable, magnetically readable, tactilely readable etc. Preferably the identifier identifies the reagent contained in the reagent container of the retaining tray (i.e. "recess reagent"), for example a primary agent. Use of disposable trays, helps to assure reagents are not cross-contaminated.

Slide retaining tray 10 generally includes a container surface 20 into which reagent recess 30 (also called "reagent container") extends from the container surface 20. In a preferred embodiment a recess reagent is deposited with the recess 30. Any type of reagent can be deposited in the recess 30, such as a primary reagent, secondary reagents, bulk reagents or combinations thereof. It should be understood that although a single reagent container 30 is illustrated, the slide tray can contain any number of reagent containers 30 as desired.

Preferably the reagent contained in the recess(es) 30 is in a matrix that is in a solid or gel form at typical ambient room temperatures (such as between 50 and 90 degrees Fahrenheit), but flowable at elevated temperatures. In one example, a primary reagent or mixture of reagents are contained within a gel base liquefiable at a temperature of 180 degrees Fahrenheit. Other phase change temperatures can be selected as desired, such as between 75 and 211 degrees Fahrenheit. Alternatively, a reagent solution can be contained within liquid solution contained within a gel cap or other container within the recess 30. Preferably the reagent containment also is heat releasable at elevated temperatures. Other elements of the slide retaining tray that will be discussed in greater detail below include for example, a flow and drip surface 40, platen 50, inlet port 60, evacuation port 70, rib 80 and examples of slide orientation tabs 90,100. It should be appreciated that multiple platens 50 and multiple reaction chambers 120 can be provided, such as illustrated in U.S. Pat. No. 5,338,358.

Slide retaining tray 10 can be formed of any material having sufficient structural strength and process neutral properties to support a slide, retain and be compatible with reagents and the temperatures employed during use. Examples include polymeric materials such as plastics or cellulosic (i.e., cellulose based or comprising) materials, metals, glass etc. One exemplary material is polyoxymethylene thermoplastic such as DELRIN (a registered trademark of E.I. DuPont de Nemours and Co. of Wilmington, Del.). The tray 10 can be formed by any process known in the art such as injection molding, machining or any other manufacturing process suitable for generating the desired features of the tray. In addition, it should be appreciated that the tray can be composed of multiple materials, such as for example, the recess region made of one material and the platen region of another.

The reagent recess(es) 30 can be of any shape, depth or orientation as desired such that the reagent(s) contained therein are directed into the reaction chamber 120 as desired during processing, and a reagent matrix can be contained within the recess 30. In the illustrated embodiment, the recess is formed at a generally lower level below container surface 20. Recess 30 includes side surfaces 610 that are illustrated as a single curved surface, and a bottom surface 620. For ease of discussion, the inside bottom surface is illustrated with reference number 620 and the opposite corresponding surface on the bottom/outside of the tray 10 is illustrated with reference number 630. As illustrated, in an embodiment, the recess side wall 610 only partially encircles the recess 30, and there is a gap 640 defined between the ends of the side wall 610. When the reagent matrix is fluidized, the reagent may flow through the gap and along the fluid flow ramp 650. Furthermore, the bottom surface 620 is generally flat, although it also can be sloped so as to promote fluid flow in any desired direction. Any other profiles also can be selected as desired, such as a stepped or curved surface.

The outside bottom surface 630 preferably is shaped and sized so as to match a corresponding heating element in a processing system, so as to best promote heat transfer from the heating element to the bottom surface 630. Efficient heat transfer between a heating element and bottom surface 630 is desired so that heat may be efficiently transferred to the inside of the recess 30 so as to fluidize reagents that are stored therein in a temperature fluidizable form, such as gels. Thus, the outside bottom surface 630 preferably is shaped in a way that promotes such heat transfer engagement, and might be relatively flat as illustrated or alternatively curved, angled or otherwise shaped.

It should be understood that the term "fluidizable" or "fluidize" as used herein can encompass any transition from one state to another, such as from a non-flowable to a flowable form, such as a liquid or viscous form, or to a gaseous form, such as when a reaction chamber can be humidity controlled. In one embodiment, a gel material becomes flowable when heated so as to transition to a substantially liquid form. It also should be noted that "liquefy" or "liquefiable" as used herein encompass any state transition properties that encompass a transition from a relatively non-flowable to a flowable state as do the terms "fluidize" or "fluidizable".

Figure 4:
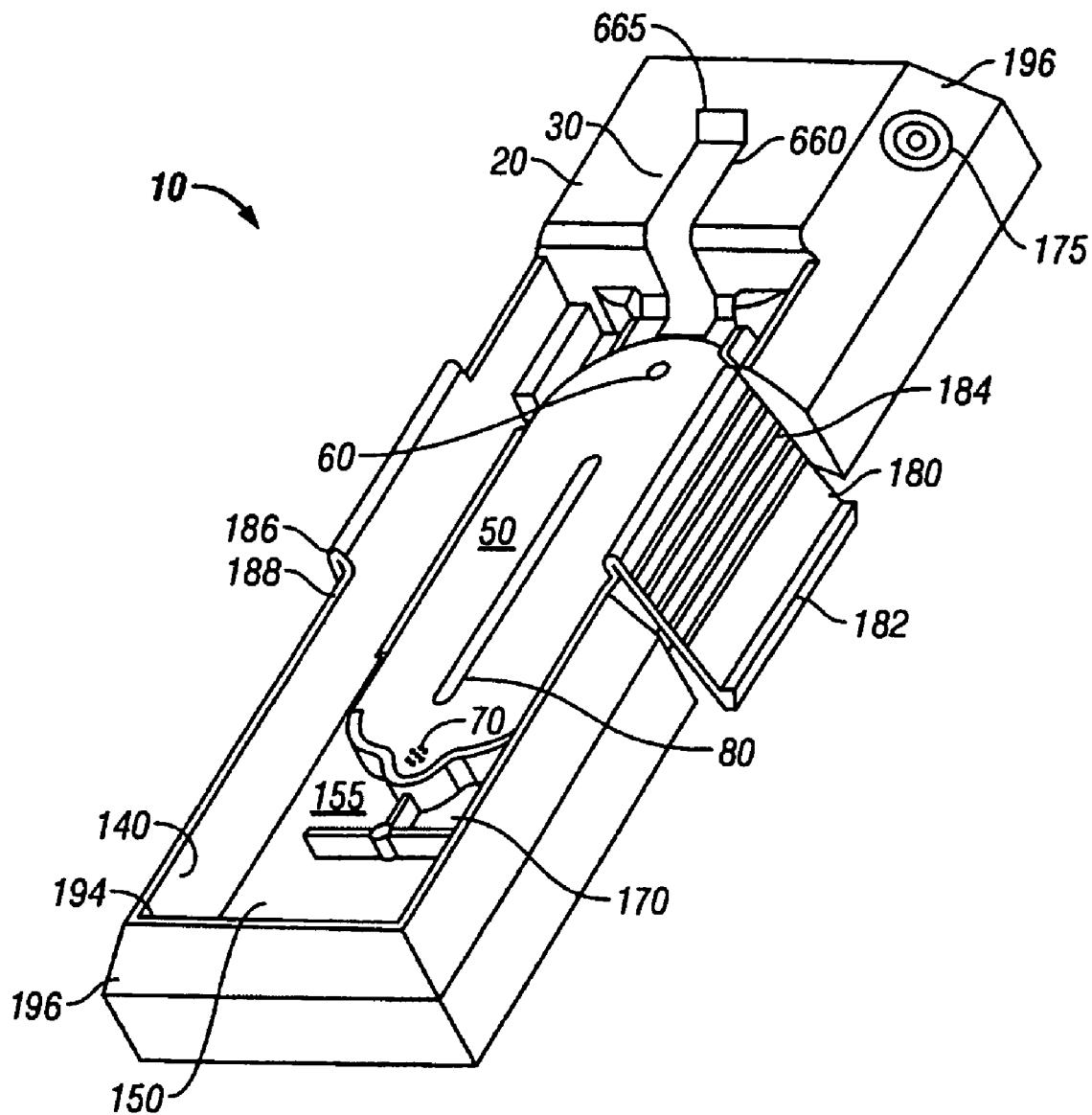
FIG. 4 is a top perspective view of a slide retaining tray with a sealed reagent recess, in accordance with the present invention.
Figure 5:
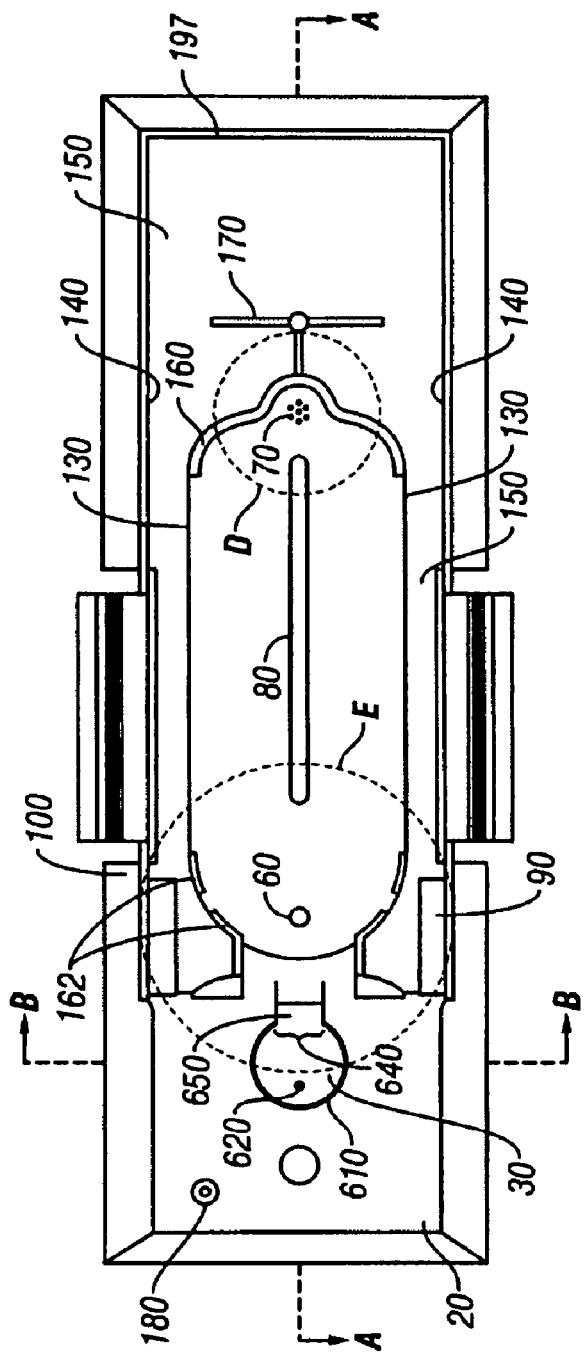
FIG. 5 is a top view of a slide retaining tray in accordance with the present invention.
Figure 7:
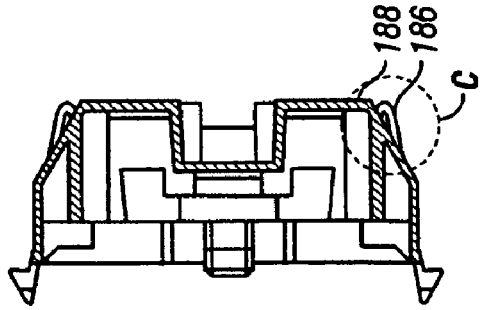
FIG. 7 is a cross-sectional view of the slide retaining tray of FIG. 5, taken along line B-B, in accordance with the present invention.
Figure 8:
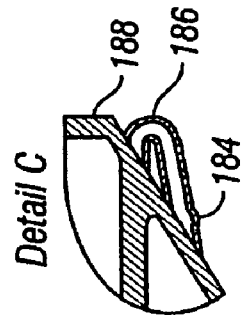
FIG. 8 is a detail view of a portion of the slide retaining tray of FIG. 7, indicated by detail C, in accordance with the present invention.
Figure 6:
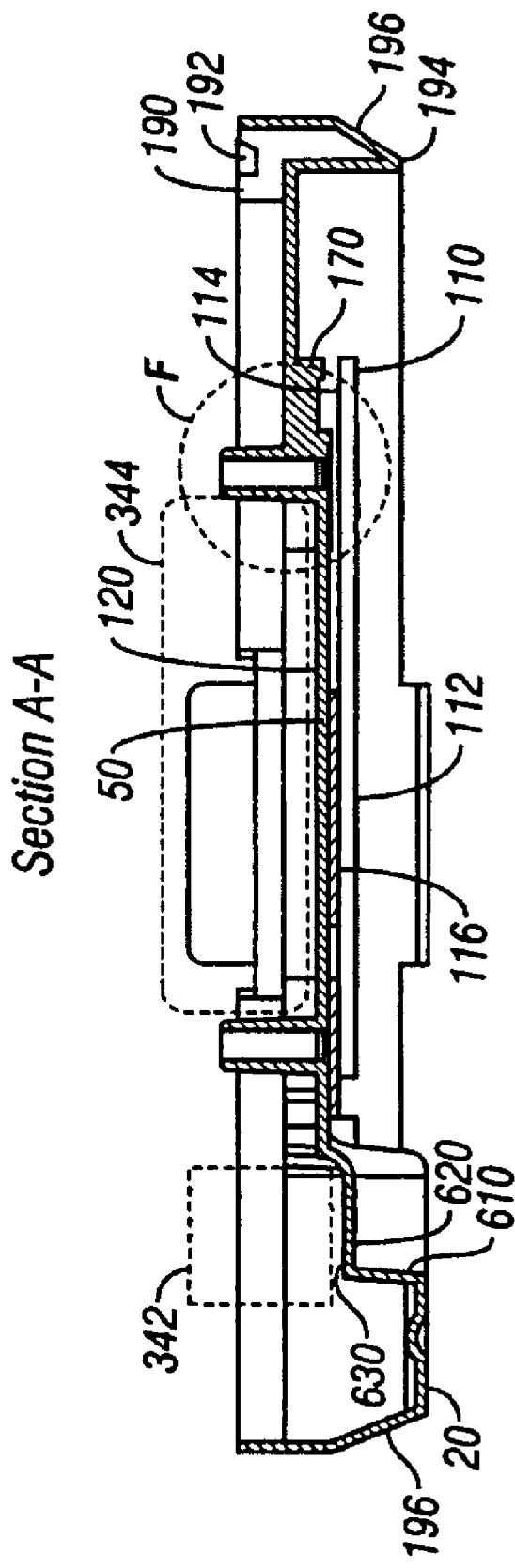
FIG. 6 is a side cross-sectional view of the slide retaining tray of FIG. 5, taken along line A-A, in accordance with the present invention.
Figure 10:
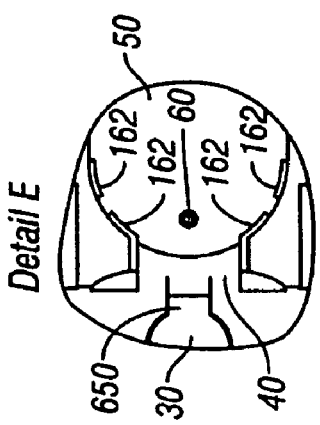
FIG. 10 is a detail view of a portion of the slide retaining tray of FIG. 5, indicated by detail E, in accordance with the present invention.
Figure 11:
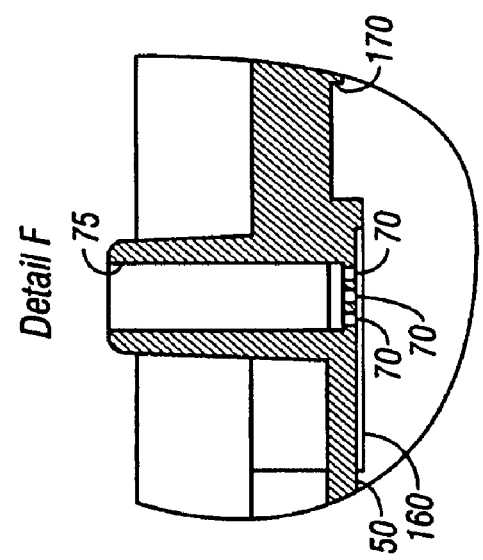
FIG. 11 is a detail view of a portion of the slide retaining tray of FIG. 6, indicated by detail F, in accordance with the present invention.
Figure 9:
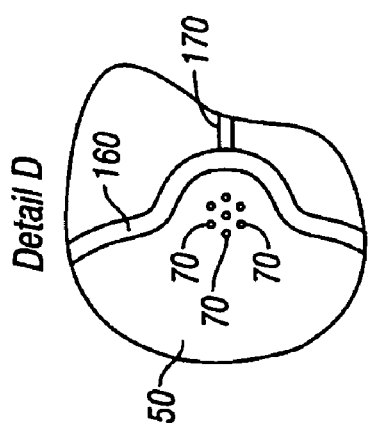
FIG. 9 is a detail view of a portion of the slide retaining tray of FIG. 5, indicated by detail D, in accordance with the present invention.

Referring to FIG. 4, an optional seal 660 (preferably removable) is provided that covers and preferably seals the recess 30, including covering and sealing the optional gap 640 and optionally also and preferably also covering the ramp 650. The seal 660 optionally includes a pull tab 665 to facilitate manual engagement and gripping of the seal so an operator may pull on and remove the seal from the retaining tray 10.

Figure 13:
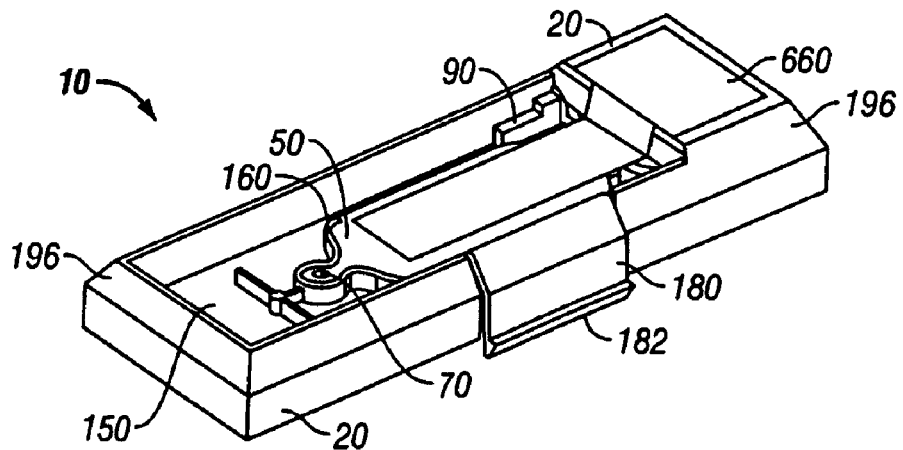
FIG. 13 is a perspective view of a slide retaining tray in accordance with the present invention.
Figure 14:
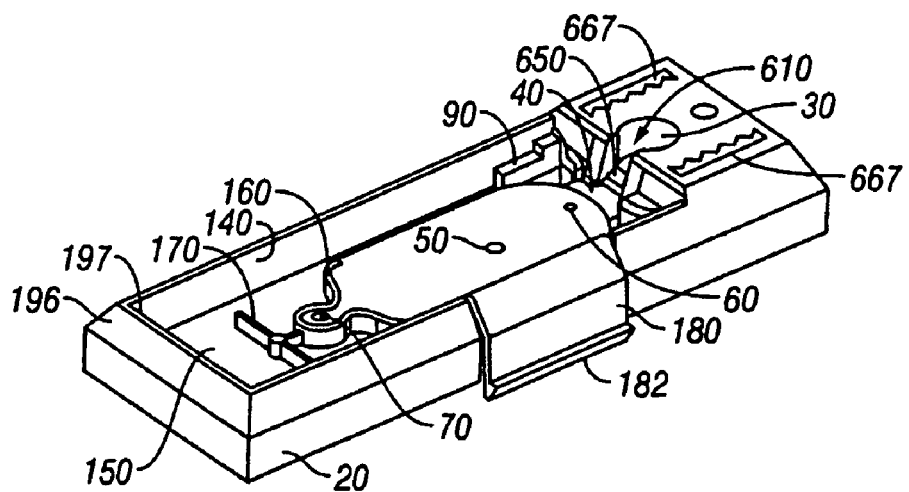
FIG. 14 is a perspective view of a slide retaining tray in accordance with the present invention.

In another embodiment, an enlarged seal 660 is provided that covers all or a portion of the platen 50 and optionally the inlet and/or evacuation ports 60, 70, as shown in FIG. 13.

Seal 660 is preferably manually removable from the slide retaining tray prior to tissue processing. For example, a user may remove the seal by grasping tab 665 and pealing seal 660 from tray 10. Although tab 665 is illustrated as being positioned at an end of the seal 660 adjacent to recess 30, it shall be appreciated that tab 665 can be positioned at any location on seal 660 such that it can be grasped by an operator. In an embodiment, portions 667 of seal 660 may remain affixed to the slide retaining tray 10 after the majority of the seal has been removed. In an alternative embodiment, a slidable barrier is provided to cover the gap 640 and/or the top of the recess 30, wherein the slidable barrier can be slid out of blocking engagement as desired, and then slid back if closure is desired.

Seal 660 may be constructed from any material that serves to cover the recess 30 and retain the material contained therein. Preferably the seal is substantially vapor impermeable so as to inhibit evaporation of the material contained within the recess 30. In one example the seal 660 is a multi-layer composite including an outer foil layer and other layers of one or more polymeric or cellulosic materials (such as a coated paper), which in turn is coated with an adhesive. The adhesive can be a contact adhesive to hold it in place, or any other form of retainer, such as other adhesives, heat seals, or mechanical seals, such as crimping. Alternatively a chemical seal can be applied by dispensing a chemical between the material in the recess 30 and gap 640 and/or the environment wherein the chemical inhibits fluid flow or vaporization.

Any number or type of reagents may be deposited into recess(es) 30. For example, reagents suitable for a potentially unlimited variety of procedures can be provided in the matrix included within one or more recesses, including immunohistochemistry procedures, staining procedures, in situ hybridization procedures, other histochemical procedures etc.

Examples of primary reagents (also called probes, markers or controls) that can be positioned either alone or in combination in recess 30 include, without limitation, any type of antibodies, probes, nucleic acids (RNA, DNA or oligonucleotides), ligands, ligand receptors, enzymes or enzyme substrates or any other molecules suitable for a desired use. The reagents can be in a natural form, purified, concentrated, diluted or otherwise conditioned. In an embodiment, the addition of signal molecules such as fluorescent dyes, enzymes, biotin, avidin, steptavidin, metals (such as silver or gold particles), dyes, stains, radioactively tagged molecules, or any other substances such as signaling or reporter molecules.

Optionally one or more secondary reagents can be included in the recess(es) 30. In a preferred embodiment, secondary reagents are dispensed from above onto a drip and flow surface of tray 10, either via a container dispensing system or pipetting system, all as discussed in greater detail below. Examples of secondary reagents that can be positioned either alone or in combination with other secondary reagents, or in combination with one or more primary reagents or bulk reagents in the recess(es) include, without limitation, any type of antibodies, probes, nucleic acids (RNA, DNA or oligonucleotides), ligands, ligand receptors, enzymes or enzyme substrates or any other molecules suitable for a desired use. The reagents can be in a natural form, purified, concentrated, diluted or otherwise conditioned. In addition, signal molecules such as fluorescent dyes, enzymes, boiotin, avidin, steptavidin, metals (such as silver or gold particles), dyes, stains radioactively tagged molecules, or any other substances such as signaling or reporter molecules may also be included.

Optionally one or more bulk type of reagent can be included in the recess(es) 30, although this is not preferred. In a preferred embodiment, bulk reagents are stored in containers and dispensed into the reaction chamber 120 of the slide retaining tray 10 via a manifold system directing the fluids into an entry port (discussed in greater detail below) of the slide tray 10. Examples of bulk reagents that can be positioned either alone or in combination with other bulk reagents, or in combination with one or more primary reagents or secondary reagents in the recess(es) include, without limitation, the following:

Tris Buffered Saline (TBS) Tween

TBS

Distilled Water

Dewaxing Solution

In one embodiment, the recess(es) 30 includes one or more apertures 670 that pass through bottom surface 620/630. Apertures 670 optionally can be used to fill or re-fill the recess 30 with a desired amount of a matrix 680 containing a reagent. After filling the recess with the reagent matrix, apertures 670 may be closed in any desired fashion, such as by applying a tape or other covering. Any other filling method or apparatus may be used to fill the recess as desired. One example is loading (or re-loading) the reagent matrix from above, into the recess 30. Such a technique has an advantage of rendering unnecessary the aperture(s) 670 on the bottom surface of the recess 30. The reagent can be positioned in the recess in any form, such as caplets, one or more pellets, liquid that is dripped into recess 30 and solidified by reducing the temperature (or gel), or gel or liquid that is poured or squeezed from a tube.

Reagent matrix 680 optionally may be formed by providing a macroscopic solid support formed of a solidified matrix material and encapsulating one or more reagents therein. The macroscopic solid support may be disintegrated to release the reagent therefrom as desired. The matrix material may be made of a material which can be broken down or decomposed by any physical or chemical process whereby the reagent can be released, such as by puncturing a structure, applying electricity, applying pressure or vacuum, or exposure to heat, electromagnetic (EM) radiation or solvents. For example, the disintegration of a gel matrix may be accomplished by liquefying the gel using heat or by dissolving the gel using a solvent.

By way of example, the matrix material may be sucrose or starch containing antibodies and decomposition may be achieved by exposing the matrix to aqueous or aqueous buffered solutions so that the matrix need not be heated if so desired. However, application of heat can decrease the time required for decomposition of the matrix and therefore may be desirable. When selecting a matrix material for a given reagent, it is desirable that the reagent and matrix material do not irreversibly bind. Moreover, when using solid or semi-solid matrices, the support material preferably is miscible with the solvent employed for the reaction procedure.

According to the present invention, supplying reagents to the reaction chamber 120 may be accomplished in a number of ways. In an example, one or more recess reagents are provided in reagent recess 30 within a gel matrix 680. The reagents can be delivered to the reaction chamber such as by melting or otherwise liquefying or dissolving the gel 680 causing the liquefied reagent to flow into gap 640 and toward the reaction chamber 120.

In the illustrated embodiment, the fluid flow passage includes fluid flow ramp 650 and drip surface 40 positioned between the reagent recess 30 and reaction chamber 120. Preferably one or both of the drip surface 40 and ramp 650 are declined towards reaction chamber 120 so as to promote gravitation force induced fluid flow towards the reaction chamber 120.

Other reagents also can be delivered either via the reagent recess(es) 30 or other devices. Likewise, the reagents can be delivered by other devices. In one example, external reagents are delivered by drop-wise application of solutions onto drip surface 40 from above. As explained in further detail below, the drop-wise application of reagents can be accomplished using an automated fluid dispensing apparatus, such as from automatically controlled pipetting systems or reagent dispensing containers. Alternatively, the drop-wise application of reagents can be performed manually. As a further alternative, reagents (or other solutions, such as washing or buffering solutions) may be provided via port 60. In such an embodiment, a fluid delivery manifold including passageways and valves may provide the fluids to port 60.

Fluid that has been introduced from recess 30, is caused to flow into the reaction chamber 120 by virtue of one or a combination of capillarity (i.e., capillary action) (such as where the fluid enters a section in which a slide 110 is positioned adjacent the platen 50), pressure differential applied via one or both of the inlet port(s) 60 and evacuation port(s) 70, vacuum pulsing, such as applied via the evacuation port(s) 70, and gravity. Gravity can be used to induce fluid flow alone, such as where the forces generated by the melting matrix 680 induce flow from the reagent recess through the gap 640 and into the reaction chamber 120. Fluid molecules at the top of the matrix 680 can have momentum via gravity. In an embodiment in which the bottom surface 620 is elevated relative to the platen 50, a ramp 650, which may be straight, curved or stepped, is provided between the bottom surface 620 of recess 30 and the drip surface 40 and/or platen 50 (in embodiments lacking a drip surface 40), whereby fluid flows down the ramp 650 from the reagent recess 30 and towards the reaction chamber 120. In another embodiment, the bottom surface 620 of recess 30 is aligned with the platen surface 50 Fluid that has been introduced via the drip surface 40 may also be caused to flow into the reaction chamber 120 by virtue of capillarity and/or gravity. In addition, fluid introduced via inlet port 60 can flow through the reaction chamber 120 by virtue of capillarity. In addition, a pressure differential between the inlet port 60 and the reaction chamber also can induce fluid flow through the reaction chamber 120. Further pressure differentials can be generated by providing a negative pressure (or vacuum) at the evacuation port 70, inducing flow in the direction of the evacuation port 70. Furthermore, features may be added to the top surface of platen, such as rib 80, to further enhance the fluid flow properties of the reaction chamber such as by maintaining reaction chamber 120 at a desired size.

After the fluid(s) introduced into the reaction chamber 120 have been within the chamber a desired amount of time, the fluid(s) remaining can be discharged via the evacuation port 70 in a similar fashion in which a negative pressure differential or vacuum is introduced via the port 70. Optionally wash fluids are introduced into the reaction chamber 120, for example by being pumped in through inlet port 60, to flush the reaction chamber 120 as desired. Evacuation port 70 optionally includes a filter (or plural small apertures) to screen or filter debris.

Platen 50 includes a generally flat surface that is the platen is elevated above a bottom surface of the tray 10. Fluid inlet port 60 is disposed at one end of the platen 50 and the evacuation port(s) 70 are preferably disposed at an opposite end of the platen 50. By spatially separating these ports on the platen 50, a pressure gradient can be introduced into reaction chamber 120 that promotes fluid flow between the inlet and evacuation ports 60, 70. As illustrated in FIG. 1, inlet port(s) 60 is situated at the end of platen 50 that is adjacent drip surface 40 and the evacuation port(s) 70 are at the opposite end. By positioning the inlet port 60 adjacent the drip surface 40, all the fluids introduced into reaction chamber 120 can be introduced from the same end (i.e. from drip surface 40 or reagent recess 340 or inlet port(s) 60) thereby promoting fluid flow in a single direction if desired. Moreover, fluid flow can further be promoted in this direction by slightly angling the slide 110 when positioned adjacent the platen 50 to form reaction chamber 120, promoting capillarity induced flow as directed by the slide angle relative to the platen.

Other fluid directing elements can be provided on the platen 50. For example a shoulder 160 may be provided at an end of the platen 50 near evacuation port 70 as shown in FIG. 1. In addition, multiple guide lips 162 may be provided at a proximal end of the platen 50. The shoulder 160 provides a lip along the distal side of the platen 50. As illustrated, shoulder 160 extends substantially around evacuation port 70 and toward the proximal end of the platen 50. In an embodiment, the top surface of the shoulder 160 is formed at substantially the same height relative to the top surface of the platen 50 as that of the tops of slide orientation tabs 90,100 or other slide orientation features at the fluid inlet end (proximal end) of the platen 50. As a result, in such an embodiment, a slide held within tray 10 will generally contact shoulder 160 and slide orientation tabs 90, 100. In another embodiment the top surface of shoulder 160 is at a different height so that the slide is angled relative to platen 50. In a still further embodiment, the slide may be positioned so that reaction chamber 120 is wider at the proximal end (near the drip surface) and thinner at the distal end. The heights of the shoulder 160 and slide orientation elements including tabs 90, 100 may be selected to provide a desired volume within reaction chamber 120. In particular greater heights of shoulder 160 and tabs 90, 100 relative to platen 50 provides a greater volume within reaction chamber 120 than relatively low heights of those features relative to platen 50. Preferably, the volume of reaction chamber 120 is selected to provide or prevent capillary action within the chamber 120 as desired, and/or to allow fluid flow caused by a pressure differential if desired. Any size reaction chamber 120 can be selected so long as a desired volume of reagent is able to flow through reaction chamber 120.

It should also be appreciated that the volume of recess 30 may be selected to correspond to the volume selected for the reaction chamber 120. For example, a larger recess volume can be selected if relatively thick tissue sections 116 are used which requires a large reaction chamber. It should be appreciated that as used herein the terms "section" and "sample" are used interchangeably and use of the term "section" is not intended to limit the application to tissue that has been cut into sections. It also should be appreciated that multiple types of slide retaining trays 10 can be used in a single processing system 200 (discussed in greater detail below). For example trays 10 having a variety of different sized recesses 30 and reaction chambers can be provided as desired. For example, tissue sections of 4 to 5 microns may be selected and an operator may select a slide retaining tray suitable for those tissue sections and different trays suitable for samples having larger or smaller section thickness.

Figure 15:
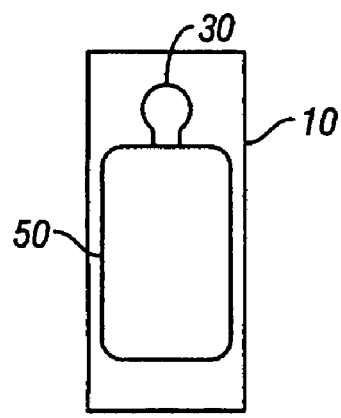
FIGS. 15-17 are top views of slide retaining trays in accordance with the present invention illustrating examples of platen shapes and sizes.
Figure 16:
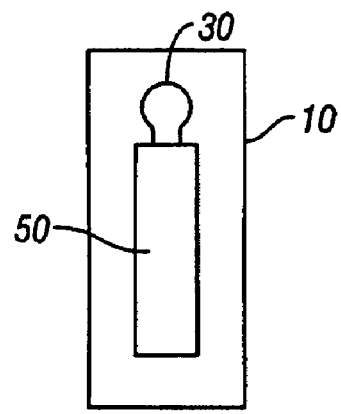
Figure 17:
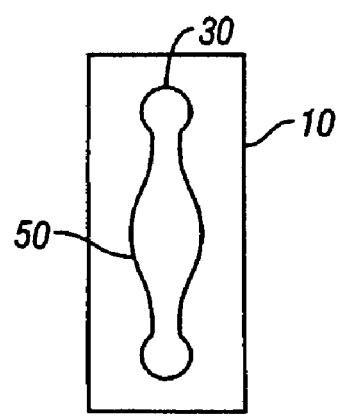

Alternatively, the volume of reaction chamber 120 may be adjusted by altering the shape of platen 50. For example, a relatively wide platen 50 is depicted in FIG. 15. A relatively narrow platen 50 is depicted in FIG. 16. In addition, a platen 50 having narrow proximal and distal portions and a wide central portion is depicted in FIG. 17. These shapes are not exclusive, and it should be understood that they are provided as examples only out of the numerous shapes that can be selected. In an example, slides having a 26 mm width are used, and a slide tray having a width between opposite inside side walls 140 of 28 mm) and a platen having a width of 24 mm is selected. It should be appreciated that selecting a slide tray having a width that is close to the width of the slide may be desirable to inhibit fluid evaporation. In a preferred embodiment, the slide tray has a width between 24 mm and 28 mm to accommodate typical microscope slides.

Preferably shoulder 160 serves to form a seal with the bottom surface 114 of the slide 110 so as to form a seal with the slide serving to inhibit vacuum leakage in that region during suction operation of the evacuation port. During tissue processing or other fluid flow, shoulder 160 helps direct fluid flow into fluid return conduit through evacuation port 70. On the underside of the tray, attachment conduits 65, 75 attach the inlet and evacuation ports, respectively, to a sample processing system that utilizes the slide retaining tray. In addition, or as an alternative, to allowing for fluid connectivity, conduits 65, 75 may serve to assist with mounting of tray 10 within a sample processing system. In a preferred embodiment, fluid connectivity is provided via the conduits 65, 75 to the respective ports 60, 70. In an embodiment, a manifold system included within a sample processing system provides tubing and valves connected to the tray via the conduits 65, 75 as discussed further herein. In an embodiment, conduits 65, 75 may be configured to have different dimensions to facilitate proper engagement with corresponding parts. In particular, the size and/or shape of conduits 65 and 75 may differ so that tray 10 may only be mounted to a sample processing system in a desired orientation. Such a difference may be used as a safeguard against improper installation.

An overflow and reagent mixing chamber 155 may be formed between the side walls 130 of the platen 50, the inside walls 140 of the tray 10, and the bottom surface 150 of tray 10. Overflow and mixing chamber 155 may be configured to retain any excess fluid that overflows from the platen 50 and reaction chamber 120. In operation, if more fluid is introduced into the tray 10 than can be retained within the reaction chamber 120, the excess can overflow into the overflow and mixing chamber 155. The overflow and mixing chamber can serve as a secondary reaction chamber or a secondary reservoir, wherein, as evaporation occurs from the reaction chamber 120 (or some fluid is evacuated via the evacuation port 70), fluid in the overflow chamber 155 may be redirected to reaction chamber 120, such as by condensation or suction provided by the evacuation port 70. In this way, fluid leaving the system via evaporation or evacuation can be replaced by fluid retained in the overflow chamber 155. As a result, the overflow and mixing chamber 155 can thereby act as a humidity regulator. In addition, different reagents may be delivered to platen 50 in deliberate excess and allowed to mix in overflow and mixing chamber 155 and then drawn back into the reaction chamber 120 by application of a vacuum to outlet port 70. It should be appreciated that overflow and mixing chamber 155 may be configured to function as one or both of an overflow chamber and a mixing chamber as desired. Overflow and mixing chamber 155 may also include an overflow drain 185 to drain excess fluid directly from overflow and mixing chamber 155.

Figure 3:
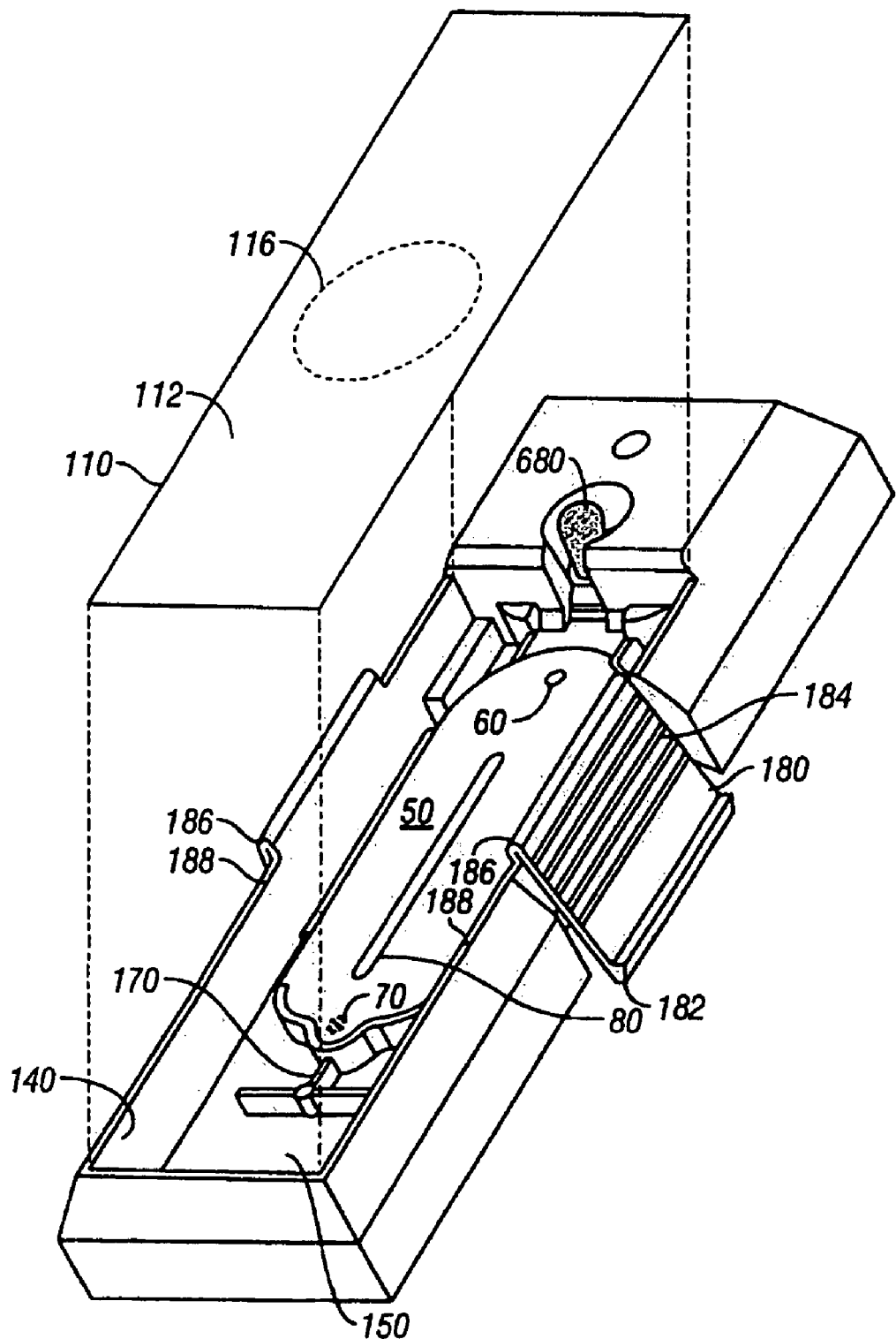
FIG. 3 is a an exploded view of a top perspective view of a slide retaining tray and slide positioned thereon in accordance with the present invention.
Figure 12:
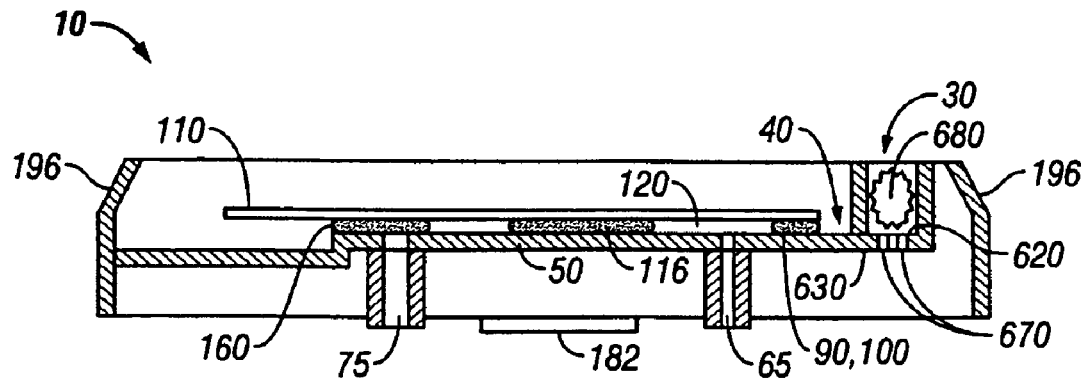
FIG. 12 is a cross-sectional view of a slide retaining tray in accordance with the present invention.

Retaining tray is configured to receive a slide 110 on top of shoulder 160 and tabs 90,100 and/or any other suitable slide orienting elements that serve to position a slide as desired within the tray 10, as shown in FIGS. 3 and 12. Preferably, the slide orienting elements create a space between slide 110 and platen to form reaction chamber 120. Slide 110 generally includes a top surface 112 and a bottom surface 114. In operation, a tissue section 116 is positioned on bottom surface 114. When slide 110 is positioned on slide retaining tray 10, the bottom surface 114 is positioned adjacent the platen 50 such that tissue section 116 is situated within reaction chamber 120, i.e. between the bottom surface 114 of the slide 110 and the top surface of the platen 50. Tissue sample 116 may be attached to the slide in any manner such that the slide and tissue sample can be positioned on the slide retaining tray 10 in the reaction chamber 120 space. In one example the tissue sample may be positioned on the slide 110 without adhesive. In an alternative embodiment, an adhesive or fluid can introduced between the section 116 and slide surface 114 to enhance surface adhesion forces.

Optionally a slide rocker 170 may be provided. In the illustrated embodiment, the slide rocker 170 is positioned adjacent the distal end of the platen 50. The slide rocker 170 can be used to assist in positioning or removing the slide from tray 10. For example, a slide positioned on the slide retaining tray 10 can be removed by an operator by pushing on an end of slide 110 adjacent the rocker. When the slide is pressed, the platen 50, or optional shoulder 160, positioned at the distal end of the platen 50 acts as a fulcrum on which the slide pivots causing the end of slide 110 adjacent to recess 30 to lift away from the slide retaining tray 10 allowing the operator to grasp the lifted end. The rocker 170 may be sized so that the lifting motion of the slide is limited as desired. The rocker preferably includes a relatively elongate top surface that the slide engages so that during the removal of slide 110 from tray 10, the lateral tilting of the slide is limited.

Slide retaining tray 10 may optionally include a machine readable identifier 175, shown in FIG. 1, that may identify the recess reagent contained within recess 30. Furthermore, any other information may be included in identifier 175 such as information regarding tissue processing tissue type, the patient and/or the doctor. Any form of machine readable identifier can be used, including physical identifiers, magnetic identifiers, radio frequency identification (RFID) identifiers, bar codes etc. In an embodiment, the identifier 175 is positioned on a top surface or a side surface of the slide retaining tray and is read optically. In another embodiment, the identifier is positioned on an underside of the tray 10.

Slide 110 optionally includes a machine readable identifier such as a bar code that may be automatically input into a processing system during any stage of processing, or via manual input. In an embodiment, a slide identifier is positioned on the top surface of the slide and may be read while an operator is applying a tissue sample 116 to the slide. In such an embodiment, when the slide 110 is positioned upside down on the slide retaining tray 10 the slide identifier may be face down and unreadable. Machine readable identifiers can be attached to the tray and/or slide in any conventional manner, for example by using an adhesive. Alternatively, machine readable identifiers may be directly printed on the tray and/or slide, or applied via heat impression.

When slide 110 has been positioned on the slide tray 10, such as being oriented by shoulder 160 and/or tabs 90, 100, a gap is formed between the undersurface 114 of the slide 110 and the platen 50, which is the reaction chamber 120 discussed herein. The tissue section 116 is disposed within the gap 120. Wash liquids such as distilled water or other rinses are pumped in through inlet conduit 65 and inlet port 60, such as via a fluid delivery manifold or any other fluid delivery system. When these wash liquids enter the reaction chamber 120, they spread as discussed previously (such as for example by capillarity) and flush the area for subsequent tissue processing steps. Waste and excess fluid are drawn through evacuation port 70 and conduit 75, and ultimately can be deposited in to a waste reservoir.

Slide tray 10 may be mounted to a mounting surface provided within a larger sample processing system by mounting tabs 180. As shown, mounting tabs 180 include angled engagement hooks 182 that are configured to be received within corresponding receiving apertures provided on the mounting surface and serve to lock the tray 10 in place. Grip surfaces 184 can be provided to promote grasping of tabs 180, and tray 10, by an operator. Mounting tabs 180 can be deformable such that an operator pushing on the tab can displace it towards the main portion of slide retaining tray 10. In this way, an operator can unlock the angled hooks 182 from the receiving apertures. Preferably, mounting tabs 180 are resilient such that after an operator deforms them they naturally return to an undeformed position.

The upper edges 186 of mounting tabs 180 can be elevated above the level of top surface 188 of the adjacent tray wall so that the graspable surface area may be enlarged. In addition, it can serve to increase the distance between grip surfaces 184 and the pivot point, thereby reducing the spring strength of the mounting tabs 180 and making it easier for an operator to disengage the slide retaining tray 10 from receiving apertures. Alternatively, the upper edges 186 of the mounting tabs 180 can be flush with or below the top surfaces 188 of the adjacent tray walls.

The underside of the tray can be sculpted in any way. It is shaped to match the corresponding heating element(s) 340, 342 and/or 344 (discussed below) so as to promote heating and cooling engagement. Alternatively, the heating elements 340, 342 and/or 344 can be selected to match the underside of the tray (such as the underside of the platen and/or the underside of the reagent recess. Likewise stacking tabs 190 can be provided. The stacking tabs promote registration of the slide trays 10 for storage or transport. In an illustrated embodiment, each of stacking tabs 190 defines a recess 192, which matches a corresponding upper edge 194 of a tray 10 when it is positioned underneath.

The top perimeter of the slide retaining tray 10 can include angled surfaces 196, or bevels, as illustrated. Angled surfaces 196 may add structural rigidity and may promote registration of stacked trays either alone or in conjunction with stacking tabs 190. In an embodiment, identifier 175 is positioned on one or more of the angled surfaces 196.

Figure 18:
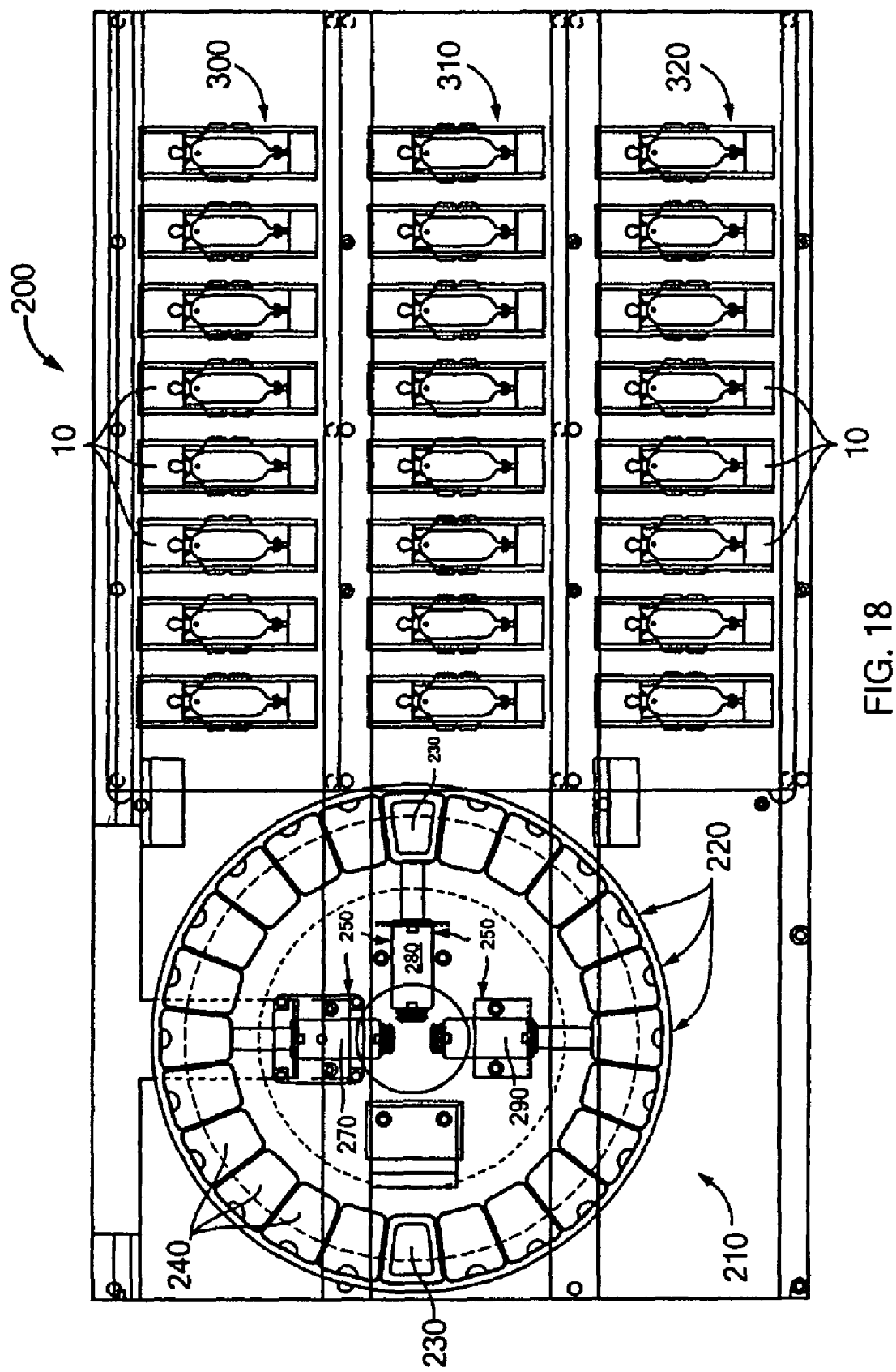
FIG. 18 is a top view of a tissue processing system suitable for use with one or more slide retaining trays in accordance with the present invention.
Figure 19:
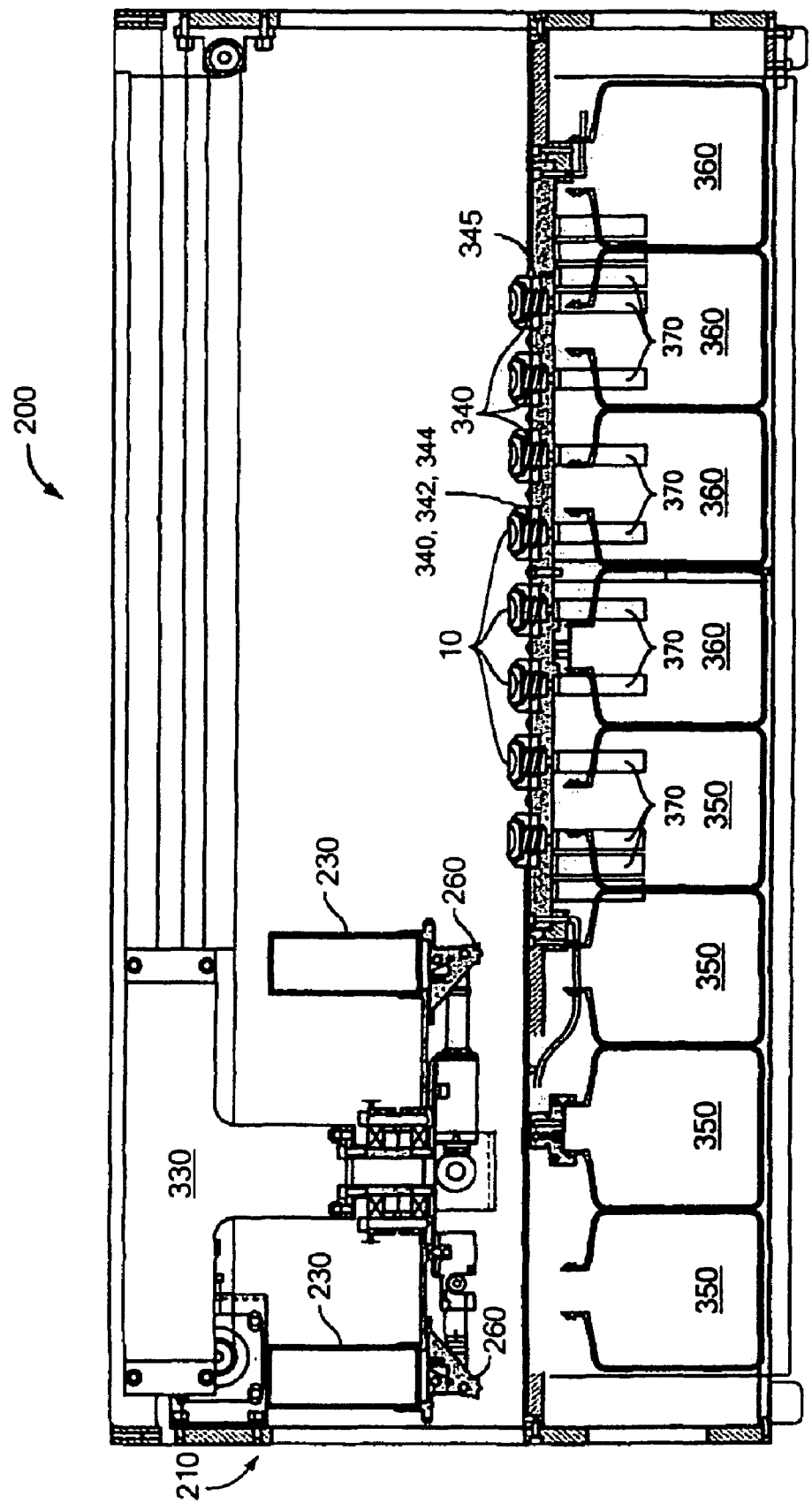
FIG. 19 is a side view of the tissue processing system of FIG. 18.

Referring to FIGS. 18 and 19, a tissue sample processing system 200 with which one or more slide retaining trays 10 may be used will now be described. The system 200 includes a fluid dispensing apparatus 210 having a plurality of stations 220 at which fluid dispensing cartridges 230 may be mounted. A fluid dispensing apparatus including a multiplicity of fluid dispensing cartridges 230 is described in U.S. patent application Ser. No. 10/639,021, the content of which is hereby incorporated by reference in its entirety. Alternatively, a fluid dispensing system using tubing or pipetting can be used as well, such as described for example in U.S. Pat. No. 5,338, 358. The stations 220 include mounting apertures 240 for selectively mounting a plurality of fluid dispensing cartridges 230. Dispensing apparatus may rotate for selectively positioning a plurality of fluid dispensing cartridges 230 adjacent to an actuator assembly 250, which is used to trigger the ejection of a desired amount of a fluid, such as a secondary reagent or a de-waxing fluid, from a reagent dispenser 260.

The slide retaining trays 10 are positioned generally beneath fluid dispensing apparatus 210 taking advantage of gravity to deliver fluids from a cartridge 230, onto the drip surface 40 of a desired slide retaining tray 10. Preferably, fluid dispensing apparatus 210 and slide retaining trays 10 are movable with respect to one another so that plural cartridges 230 can be positioned to dispense fluids on any desired tray 10. Any combination of movability of the fluid dispensing apparatus 210 and the slide retaining trays 10 may be selected. For example, both may be movable or only one may be movable and the other stationary. The retaining trays 10 may all support the same type of item, such as slides, or they may be configured to support alternative types of items such as slides and containers.

In an example of operation of the tissue processing system 200, the fluid dispensing apparatus 210 is rotated so that individual cartridges 230 are selectively positioned adjacent actuator assembly 250. Alternatively, an actuator assembly may be positioned adjacent to each cartridge 230 such that rotation of the fluid dispensing apparatus 210 is not required. The actuator assembly 250 may be any activation device that triggers the cartridge 230 to emit a controlled amount of fluid. Preferably, the fluid dispensing apparatus may be both translated and rotated with respect to the slide retaining trays 10 so that an individual cartridge 230 can be selectively positioned above any tray 10. Once the cartridge 230 is positioned above a slide retaining tray 10, actuator assembly 250 triggers the cartridge 230 to emit a controlled amount of fluid onto the tray 10.

Actuator assembly 250 optionally includes three actuators 270, 280, 290 which may be used to dispense fluid onto three rows 300, 310, 320 of receiving members, respectively. In operation, actuator 270 is adapted to dispense fluids onto slide retaining trays 10 disposed in row 300, actuator 280 is adapted to dispense fluids onto slide retaining trays 10 disposed in row 310 and actuator 290 is adapted to dispense fluids onto slide retaining trays 10 disposed in row 320. Of course, as will be understood by those of skill in the art, any number of actuators and/or slide retaining trays can be employed without departing from the scope of the present invention.

Referring to FIG. 19, in a preferred embodiment the fluid dispensing apparatus 210 is rotatably attached to a support member 330 such that the cartridges 230 can be rotated with respect to the actuator assembly 250. Actuator assembly 250 is fixedly attached to the support member 330, optionally beneath fluid dispensing apparatus 210. Preferably, support member 330 is configured such that the cartridges 230 can be both rotated and translated with respect to the trays 10. In this manner, any cartridge 230 can be selectively positioned above any slide retaining tray 10.

Slide retaining trays 10 preferably are mounted on spring loaded heating/cooling pads 340, thereby providing selective and/or independent heating and/or cooling of the slides. Additionally, heating/cooling pads 340, 342, 344 are capable of independently heating the plateau or platen region and the recess region. In an embodiment, each tray has a corresponding heating and/or cooling element 340, maintaining the tray at a particular desired temperature. In an alternative embodiment, there are two or more heating and/or cooling elements for each tray. In one embodiment, a heating and/or cooling element 342 is provided adjacent the outside bottom surface 630 of the reagent recess 30 and another heating and/or cooling element 344 is provided adjacent the outside bottom surface of the platen 50. In such an embodiment, the recess and the platen can be maintained at different temperatures. In operation, the recess element 342 can elevate the recess 30 to a particular desired temperature at which a reagent containing matrix 680 within the recess 30 is elevated above a flow temperature and the material begins to flow as desired toward the platen 50. Once the reagent flows, if a second reagent is contained in a second matrix 680 in the recess, which has a different (such as higher) flow temperature, or if a second reagent is contained in another recess 30, the heating element 342 can be operated to raise the temperature to the desired level to liquefy the second matrix. It should be appreciated that multiple heating elements 342 can be provided to simultaneously or sequentially, or otherwise, provide different heating/cooling properties and regulate the reaction kinetics of the reagent(s) as desired. The heating element(s) 342 also can be operated to cool the recess 30, such as to counteract heat generated by the instrument during operation. In one example the instrument generates sufficient heat to fluidize the reagent in the recess 30 in the absence of cooling via element(s) 342. Also in operation the platen can be heated as desired, either using a single element or one or more specialized platen heating and/or cooling element 344. In this way the temperature of the reaction chamber 120 can be controlled as desired. For example reactions can be accelerated or slowed depending on the temperature maintained. Generally speaking, the reaction kinetics are regulated in this way. Other heating/cooling elements can be provided to provide localized heating to the tray 10 as desired as well.

Preferably a temperature controlling system is provided that controls the heating and/or cooling elements 340, 342, 344 as desired. In one alternative, a feedback control is provided whereby temperature sensor(s) detect the temperature at desired locations and provide feedback information to the controller, which in turn uses that information to control the operation of the heating and/or cooling elements. For example, the sensors can be positioned to detect temperatures at or near any of the platen 30, recess 50 outside bottom surfaces of the recess or platen, the gap 640, fluid flow ramp 650 etc. According to some embodiments, the reagent containing matrix 680 is initially cooled within recess 30, then heated to liquefy the matrix 680 and form a flow.

Tissue processing system 200 optionally includes supply containers 350, drain containers 360 and a fluid delivery manifold 370. Supply containers 350 can be used to hold liquids such as water for rinsing or flushing the gap between the slides and the plateau. Fluid delivery manifold 370 preferably includes valves and switches for directing the flow of fluids supplied through fluid inlet port 60 and conduit 65. In addition, the fluid delivery manifold includes valves and switches for directing the flow of excess fluids and waste material from fluid evacuation ports 70 and conduits 75 into drain containers 360.

Figure 20:
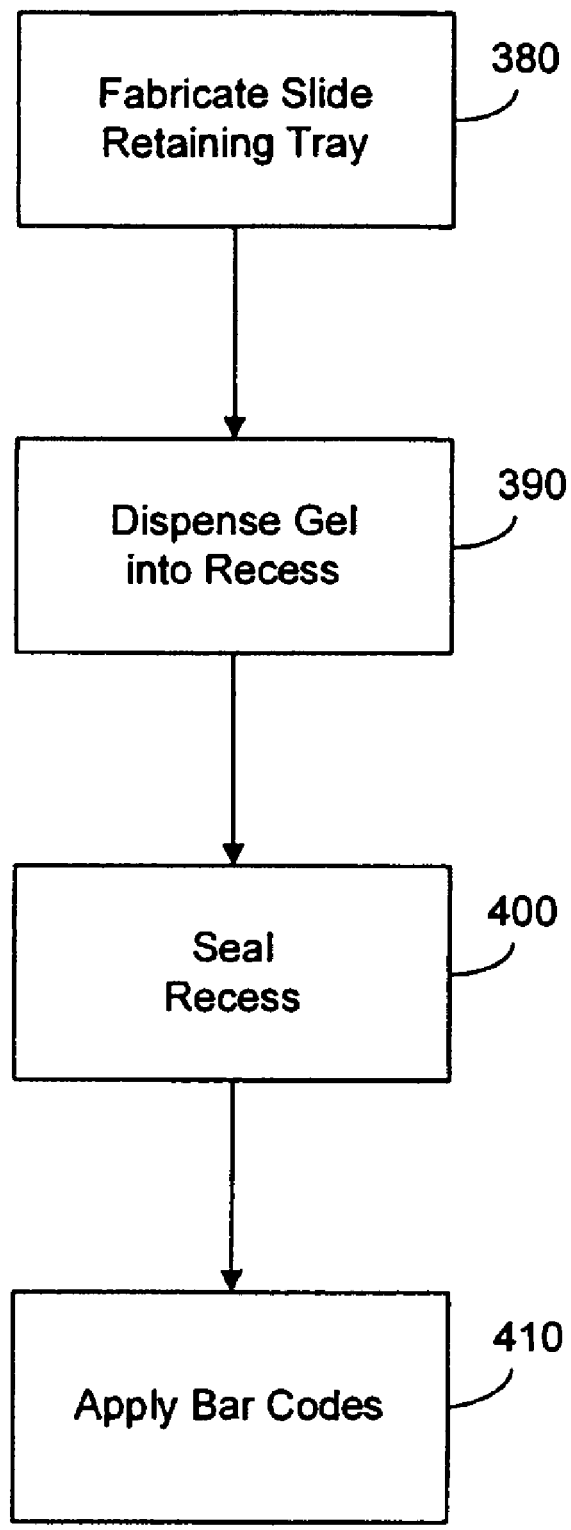
FIG. 20 is a flowchart depicting a method of manufacturing a slide retaining tray in accordance with the present invention.

A method of manufacturing a slide retaining tray 10 according to the principles of the present invention will now be described with respect to FIG. 20. As illustrated diagrammatically as box 380, the initial step involves fabricating the slide retaining tray 10. According to a preferred embodiment, slide tray 10 is fabricated from a polymeric material that is injection molded to form the desired structural shape. However, as would be understood to those of ordinary skill in the art, any fabrication process can be used or material selected that can provide the desired structural features, without departing from the scope of the present invention.

Referring to box 390, the next step involves dispensing a desired quantity of gel into the gel retaining areas, such as recess 30. For example, a predetermined amount of gel 680 may inserted through apertures 670 in the bottom surface 620 of recess 30, or alternatively gel 680 can be inserted from above. After filling the recess 30, optional apertures 670 may be sealed by applying a tape or other covering. As illustrated diagrammatically as box 400, the next step involves sealing the recess 30. Any form of seal can be selected that can retain the gel in place and reduce vaporization and/or fluidic flow loss. For example, a mechanical seal (such as seal 660) can be applied as discussed above. Referring to box 410, the next step involves optionally applying identifiers 175 to the slide retaining tray 10.

Figure 21:
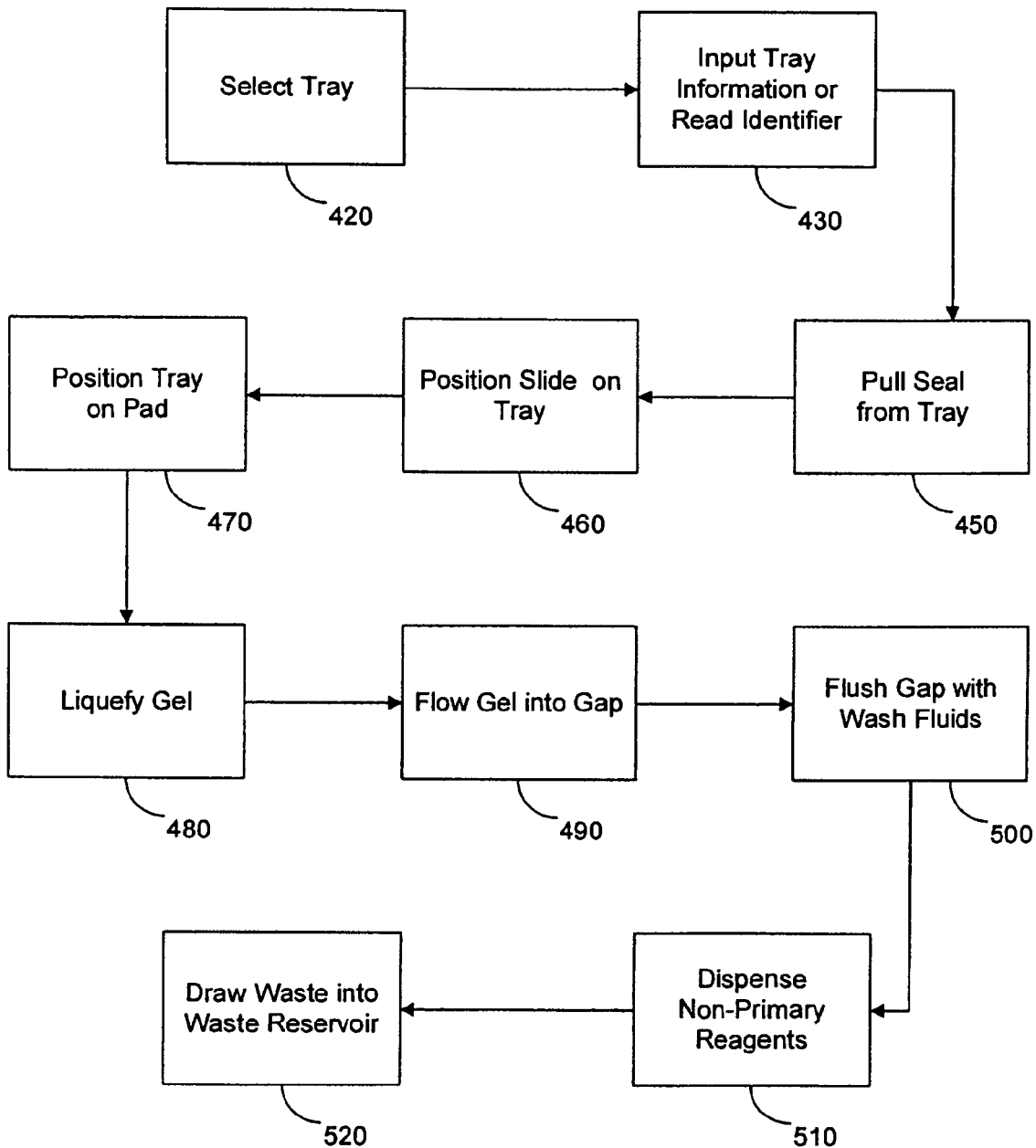
FIG. 21 is a flowchart depicting a method of using a slide retaining tray in accordance with the present invention.

An example of a method of using a slide retaining tray 10 in accordance with the principles of the present invention will now be described with respect to FIG. 21. As illustrated diagrammatically as box 420, the initial step involves selecting a slide retaining tray 10 based upon the type of gel or reagent(s) contained therein. Of course, the type of gel (i.e. reagent) contained within an individual tray 10 is dependent upon the type of test to be performed on the tissue sample 116. In other words, the initial step of selecting a slide retaining tray 10 may include the step of determining the type of test to be performed on the tissue sample 116.

As illustrated diagrammatically as box 430, the next step involves optionally entering data concerning the reagent, tray etc. For example, optionally an identifier on the tray is read, such as for example swiping a bar code. Other ways of identifying the tray also might be used, such as machine identifiable tray features such as protrusion patterns or sizes, shapes etc. The tray identifier optionally identifies the reagent(s) contained in the tray. Alternatively, the identifying information can be input into a memory associated with the processing system such as via manual input via a keyboard or oral input such as via voice recognition software. In an optional embodiment, slide information can be input as well, such as via keyboard input, voice recognition input, machine identifier or shape. As discussed previously, the slide may be positioned face down on the tray 10, and accordingly, an identifier preferably is not read when the slide is positioned on the tray or in a processing instrument. In an alternative embodiment the slide identifier can be read after the slide is positioned on the tray.

As illustrated diagrammatically as box 450, the next step involves pulling the seal 190 from the tray 10 in embodiments where a seal might be used, thereby exposing recess 30. Referring to box 460, the next step involves positioning a slide 110 on the tray 10. Preferably, the slide 110 is positioned such that tissue sample 126 is disposed between the slide 110 and the platen 50 (i.e. plateau 50). As illustrated diagrammatically as box 470, the next step involves optionally positioning the slide retaining tray 10 on a spring loaded heating/cooling pad 340, 342, 344.

As illustrated diagrammatically as box 480, the next step involves liquefying the reagent matrix 680 (i.e. the gel). This step may include the step of heating to form a melt. Alternatively, the matrix 680 may be soluble in a solvent, which is added to recess 30 to dissolve it. Thus, the step of liquefying the matrix 680 alternatively may include the step of dissolving gel 680 using a solvent. It shall be appreciated that the tray may be heated prior to liquefying reagent matrix 680 to temperatures below the melting temperature of the matrix. In an embodiment, tray 10 may be heated to approximately 100° C. prior to liquefying reagent matrix 680.

Referring to box 490, the next step involves flowing the liquefied reagent containing matrix over drip surface 40 into the gap 120 between the platen 50 and the slide 110. This step may be accomplished with the assistance of gravity. Referring to box 500, the next step optionally involves flushing the gap 120 with wash fluids to prepare the tissue sample for subsequent tissue processing steps. It shall be appreciated that the wash fluids may be drawn into a waste reservoir as shown in step 520 prior to performing the next step of dispensing non-primary reagents. As illustrated diagrammatically as box 510, the next step involves optionally dispensing reagents from a fluid dispensing apparatus 210 onto the drip surface 40. Referring to box 520, the next step involves drawing waste and excess fluid through the fluid return conduit (i.e. evacuation port 70, and conduit 75) into a waste reservoir. It shall be appreciated that waste fluids may be drawn through the fluid return conduit and into a waste reservoir after each step of filling the reaction chamber. With further reference to FIG. 21 the steps illustrated by boxes 430, 450, 460, 470 may be performed in any order without departing from the scope of the present invention. Additionally, the step of inputting tray information 430 can optionally be performed after the step of positioning the slide 110 on the tray 10 (box 460). Further, the step of pulling the seal 190 from the tray 10 (box 450) can be performed at any time after the initial step of selecting a tray 10 based upon the type of gel contained therein. Additionally, steps 480, 490, 500, 510 and 520 may be performed in any order. In particular, it shall be appreciated that a non-primary reagent may be dispensed prior to liquefying the gel, and a step of flushing the gap and/or drawing waste into a waste reservoir may be performed after any step of introducing a material into the gap.

Thus, it is seen that a slide retaining tray for processing a substrate is provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

What is claimed is:

1. A sample retaining tray comprising:
   a reagent holding portion that defines a reagent retaining recess;
   a sample holding portion having opposing sidewalls that define a platen that includes a reagent surface that defines an inlet port and an outlet port;
   a fluid flow portion that is configured to place the reagent recess in fluid communication with the reagent surface; and
   a chamber dimensioned to receive a slide between opposing sidewalls and a bottom surface defining the chamber, wherein a difference between the opposing side walls of the sample holding portion and the opposing sidewalls of the chamber define a reservoir that is in bi-directional fluid communication with the reagent surface.

2. The sample retaining tray of claim 1 further comprising a reagent within the reagent retaining recess.

3. The sample retaining tray of claim 2 wherein the reagent within the reagent retaining recess is contained within a fluidizable matrix.

4. The sample retaining tray of claim 1 wherein the flow portion includes a drip surface that is in fluid communication with the reagent surface that is configured to receive a fluid dispensed from above.

5. The sample retaining tray of claim 4 wherein the drip surface is located between the reagent retaining recess and the platen.

6. The sample retaining tray of claim 1 further comprising at least one slide positioning element configured to position a microscope slide within the sample retaining tray such that the microscope slide is spaced above the reagent surface thereby forming a reaction chamber between the slide and the platen.

7. The sample retaining tray of claim 6 wherein the slide positioning element is configured to hold a slide such that a bottom surface of the slide is angled relative to the reagent surface of the platen.

8. The sample retaining tray of claim 6 further comprising a tissue section positioned within the reaction chamber.

9. The sample retaining tray of claim 1, further comprising a side wall having an angled upper surface and a machine readable identifier positioned on the angled upper surface, the machine readable identifier configured to provide information regarding a reagent contained within the reagent recess.

10. The sample retaining tray of claim 2 further comprising a seal positioned over the reagent recess.

11. The sample retaining tray of claim 1 further comprising a screen on the outlet port.

12. The sample retaining tray of claim 1, wherein the platen includes a shoulder extending upward from the reagent surface of the platen at a distal end of the platen.

13. The sample retaining tray of claim 12 further comprising a rocker positioned adjacent the distal end of the platen, the rocker including a top surface at a lower level relative to the shoulder.

14. A sample processing system, comprising:
   a plurality of sample retaining trays, wherein each tray includes:
      a reagent holding portion that defines a reagent retaining recess;
      a sample holding portion having opposing sidewalls that define a platen that includes a reagent surface that defines an inlet port and an outlet port;
      a fluid flow portion that is configured to place the reagent recess in fluid communication with the reagent surface; and
      a chamber dimensioned to receive a slide between opposing sidewalls and a bottom surface defining the chamber, wherein a difference between the opposing side walls of the sample holding portion and the opposing sidewalls of the chamber define a reservoir that is in bi-directional fluid communication with the reagent surface;
   a manifold in fluid communication with the sample retaining trays;
   a heating and/or cooling system in thermal communication with the sample retaining trays; and
   an external reagent dispensing system in fluid communication with the sample retaining trays.

15. The sample retaining tray of claim 1, further comprising:
   an identifier positioned on a surface of the sample retaining tray.

16. The sample retaining tray of claim 15, wherein the identifier is a machine readable identifier comprising information regarding a sample held within the sample holding portion of the sample retaining tray.

17. The sample retaining tray of claim 15, wherein the identifier comprises information regarding a reagent contained within the reagent recess, information regarding sample processing or information regarding a sample type.

18. The sample retaining tray of claim 1 further comprising:
   a mounting mechanism for releasably securing the sample retaining tray to a mounting surface.

19. The sample retaining tray of claim 18, wherein the mounting mechanism comprises a mounting tab extending from a surface of the tray and an engagement hook dimensioned to be received within a corresponding receiving aperture of the mounting surface.

20. The sample retaining tray of claim 1 wherein the inlet port and the outlet port defined by the reagent surface extend through the reagent surface to an opposite side thereof.

21. The sample retaining tray of claim 1 wherein the opposing sidewalls, the platen and the reagent surface are integrally formed.

* * * * *